(12) United States Patent
Sugimoto et al.

(10) Patent No.: US 6,663,561 B2
(45) Date of Patent: Dec. 16, 2003

(54) VIDEO ENDOSCOPE SYSTEM

(75) Inventors: Hideo Sugimoto, Tokyo (JP); Takayuki Enomoto, Saitama-ken (JP); Ryo Ozawa, Tokyo (JP)

(73) Assignee: Pentax Corporation, Tokyo (JP)

( * ) Notice: Subject to any disclaimer, the term of this patent is extended or adjusted under 35 U.S.C. 154(b) by 0 days.

(21) Appl. No.: 09/968,917

(22) Filed: Oct. 3, 2001

(65) Prior Publication Data
US 2002/0042556 A1 Apr. 11, 2002

(30) Foreign Application Priority Data

Oct. 5, 2000 (JP) .......................................... 2000-306430
Oct. 18, 2000 (JP) .......................................... 2000-317847

(51) Int. Cl.[7] ................................................. A61B 0/06
(52) U.S. Cl. .......................................... 600/160; 600/178
(58) Field of Search ................................. 600/160, 178, 600/181, 476, 478

(56) References Cited
U.S. PATENT DOCUMENTS

| | | | | |
|---|---|---|---|---|
| 5,001,556 A | * | 3/1991 | Nakamura et al. | ............ 358/98 |
| 5,430,476 A | * | 7/1995 | Hafele et al. | ................. 348/70 |
| 5,749,830 A | * | 5/1998 | Kaneko et al. | ............. 600/160 |
| 6,099,466 A | | 8/2000 | Sano et al. | |
| 6,422,994 B1 | * | 7/2002 | Kaneko et al. | ............. 600/160 |

* cited by examiner

Primary Examiner—Aaron Roane
(74) Attorney, Agent, or Firm—Greenblum & Bernstein, P.L.C.

(57) ABSTRACT

A light transmitting part is formed on a second rotary shutter to intermittently transmit excitation light emitted from an excitation light source, which has a circumferential length substantially equal to a half of the entire periphery of the second rotary shutter in order to extend the period during which excitation light is emitted through a light distribution lens. As a living tissue is irradiated with excitation light, it generates autofluorescence. Although the autofluorescence is weak, a CCD can convert the image of the object under examination formed from the autofluorescence into a fluorescence video signal of a sufficient intensity level because excitation light is irradiated for an extended period of time. The obtained fluorescence video signal does not need to be amplified to an undesirable extent and hence can be processed with a high S/N to provide an appropriate diagnostic video signal that is free from noise.

15 Claims, 16 Drawing Sheets

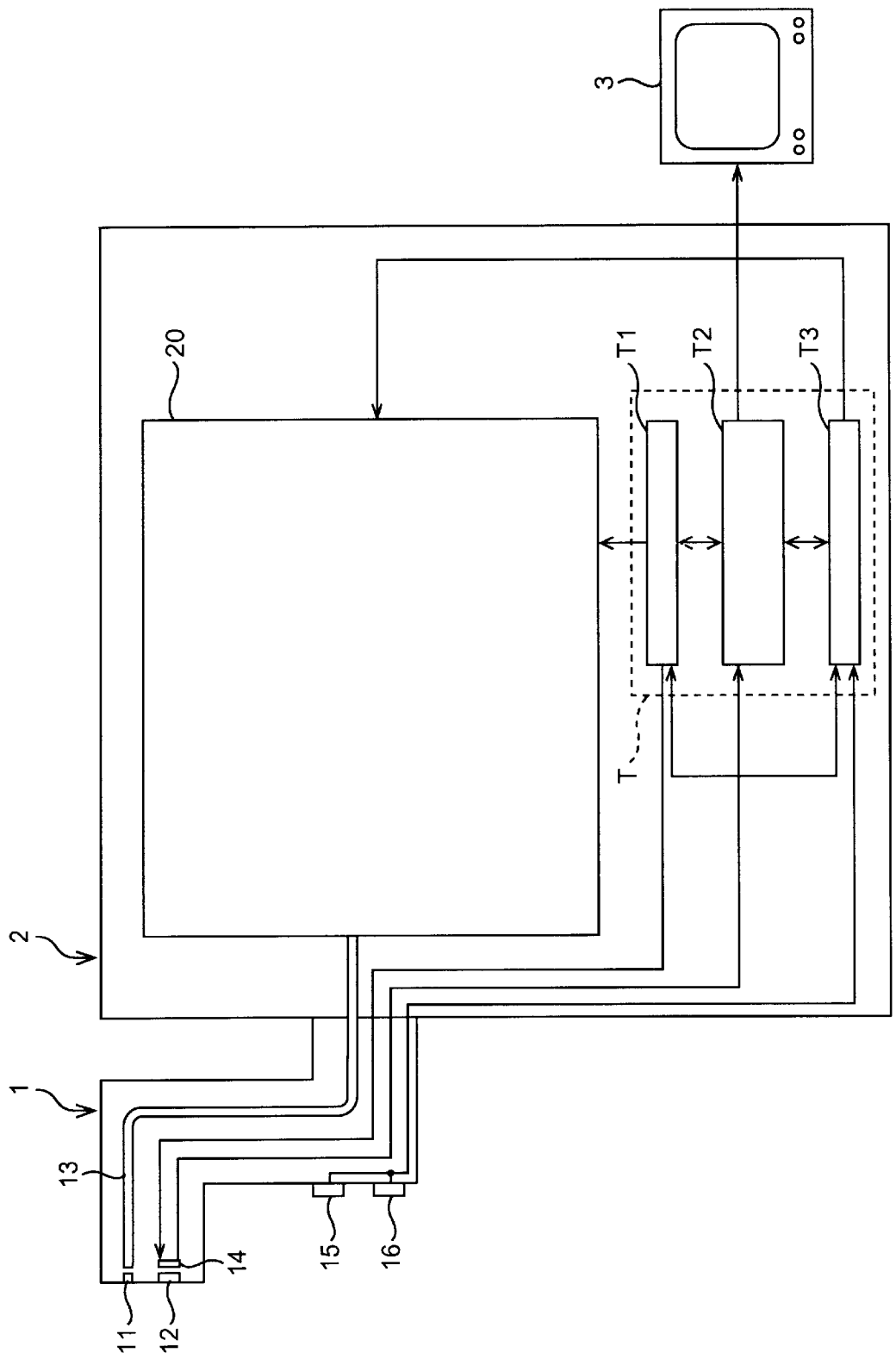

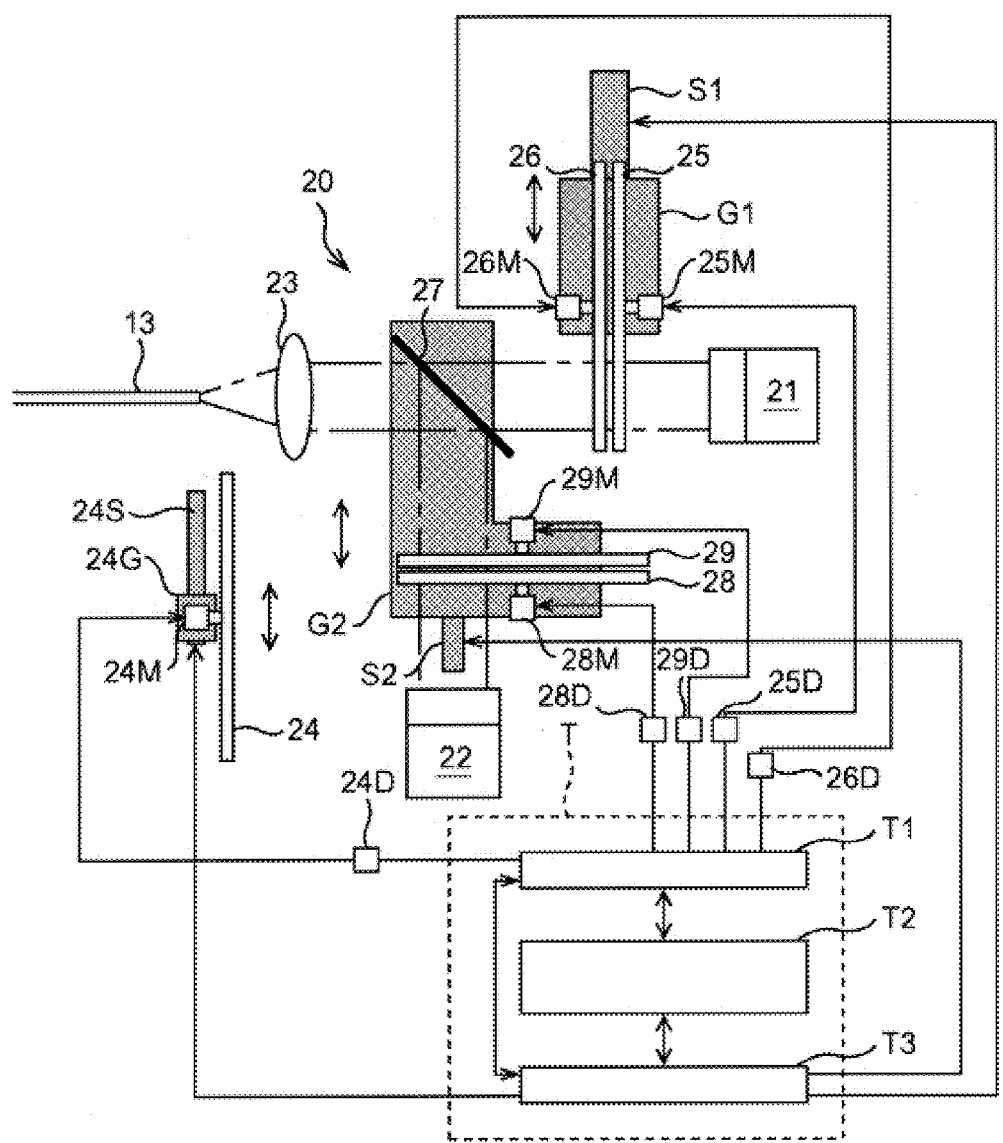

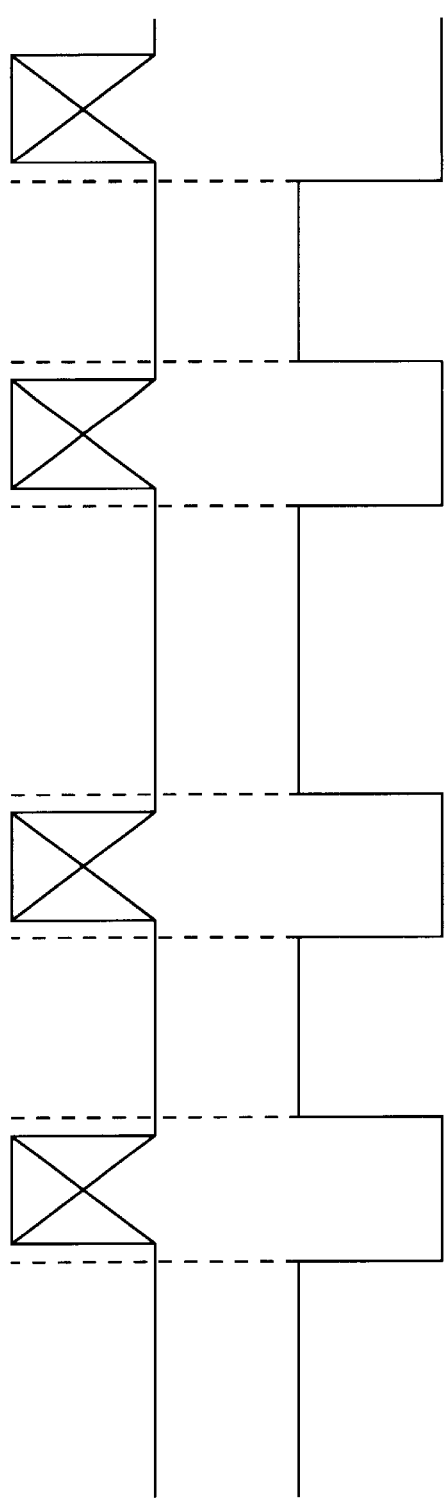

VIDEO ENDOSCOPE SYSTEM

BACKGROUND OF THE INVENTION

1. Field of the Invention

This invention relates to a video endoscope system that enables an object to be observed through autofluorescence caused from a living body.

2. Description of the Related Art

Video endoscope system for obtaining a color image of an object under examination, for example a coelomic wall of the living body and the like, are known and being utilized. RGB frame sequential system is also known as method for obtaining a color image of an object under examination. The RGB frame sequential system is adapted to obtain a color video signal by synthetically combining monochromatic video signals obtained separately while the object under examination is being irradiated with blue, green and red light, respectively.

Besides, video endoscope systems enable a living body to be observed through fluorescence (i.e., autofluorescence) generated from the living body when the living body is irradiated with excitation light. The autofluorescence generated from diseased tissue is weaker than the autofluorescence generated from healthy tissue. Therefore, an operator can explore the object under examination through the autofluorescence generated from the object and recognize an area where the autofluorescence is weak as a diseased area.

Recently, video endoscope systems that are adopted with the RGB frame sequential system and incorporated with the functional feature of fluorescence observation have been proposed. Such a video endoscope system can display both an ordinary moving color image of an object under examination and a moving fluorescent image of the object based on the autofluorescence generated from the object. Therefore, the operator using the video endoscope system can selectively acquire either the ordinary moving color image of the object or the moving fluorescent image of the object based on the autofluorescence generated from of the object. Such a video endoscope system has a light source unit for emitting light with which the object is irradiated, and a CCD for picking up an image of the object that is illuminated with the light. When the video endoscope system is operating in the ordinary observation mode, the light source unit emits blue, green and red light sequentially and repeatedly. When, on the other hand, the video endoscope apparatus is operating in the fluorescence observation mode, the light source unit emits excitation light and white light alternately and repeatedly.

FIG. 19 is a timing chart for illumination of light emitted from the light source unit and processes of image acquirement by the CCD. Firstly, the operation of the video endoscope system in the ordinary observation mode will be described by referring to FIG. 19A and FIG. 19B. FIG. 19A shows the operation of the CCD in the ordinary observation mode and FIG. 19B shows the periods in which illumination light emitted from the light source unit is irradiated in the ordinary observation mode. A "B irradiation" period during which blue light is emitted from the light source unit corresponds to a "B accumulation" period for the CCD, which means that an electric charge corresponding to the image of the object formed from blue light is accumulated in each pixel of the CCD when the object under examination is irradiated with blue light. The electric charge accumulated in the "B accumulation" period is output as B video signal in a "B transfer" period that comes immediately after the "B accumulation" period. The "G accumulation" period that comes immediately after the "B transfer" period corresponds to a "G irradiation" period during which green light is emitted from the light source unit, which means that an electric charge corresponding to the image of the object formed from green light is accumulated in each pixel of the CCD during the "G accumulation" period. The electric charge accumulated in the "G accumulated period is output as G video signal in a "G transfer" period that comes immediately after the "G accumulation" period. The "R accumulation" period that comes immediately after the "G transfer" period corresponds to an "R irradiation" period during which red light is emitted from the light source unit, which means that an electric charge corresponding to the image of the object formed from red light is accumulated in each pixel of the CCD during the "R accumulation" period. The electric charge accumulated in the "R accumulation" period is output as R video signal in an "R transfer" period that comes immediately after the "R accumulation" period. Then, a color video signal representing a color image of the object under examination is synthesized from the B video signal, the G video signal and the R video signal output sequentially from the CCD.

Next, the operation of the video endoscope system in the fluorescence observation mode will be described with reference to FIG. 19C and FIG. 19D. FIG. 19C shows the operation of the CCD in the fluorescence observation mode and FIG. 19D shows the periods in which illumination light emitted from the light source unit is irradiated in the fluorescence observation mode. The object under examination generates autofluorescence as it is irradiated with excitation light (ultra violet light). Then, the CCD picks up the image formed from the autofluorescence generated from the object. Thus, a "UV irradiation" period during which the excitation light (ultra violet light) is emitted from the light source unit corresponds to an "F accumulation" period for the CCD, which means that an electric charge corresponding to the image of the object formed from the autofluorescence generated from the object is accumulated in each pixel of the CCD when the object under examination is irradiated with the excitation light. The electric charge accumulated in the "F accumulation" period is output as F video signal in an "F transfer" period that comes immediately after the "F accumulation" period. A "W irradiation" period during which white light is emitted from the light source unit corresponds to a "W accumulation" period of the CCD, which means that an electric charge corresponding to the image of the object formed from the white light is accumulated in each pixel of the CCD when the object under examination is irradiated with the white light. The electric charge accumulated in the "W accumulation" period is output as W video signal in a "W transfer" period that comes immediately after the "W accumulation" period. A video signal as to the object to be used for diagnosis is synthesized from the F video signal and the W video signal output from the CCD. More specifically, the video signal of the object, to be used for diagnosis is obtained by subtracting the F video signal from the W video signal.

In the above described video endoscope system, the "W irradiation" period is as long as the "UV irradiation" period, as shown in FIG. 19D. Therefore, the "W accumulation" period is as long as the "F accumulation" period, as shown in FIG. 19C. Now, the autofluorescence generated from the object is very weak. Therefore, when obtaining a video signal to be used for diagnosis is generated from a W video signal and an F video signal, the F video signal needs to be greatly amplified. However, as the amplification factor is increased, the S/N ratio of the F video signal falls and the video signal to be used for diagnosis which is ultimately obtained may contain a high level of noise.

SUMMARY OF THE INVENTION

In view of the above identified circumstances, it is therefore the object of the present invention to provide a video endoscope system which is adapted to obtain an image to be used for diagnosis, without lowering the S/N ratio.

In the first aspect of the present invention, the above object is achieved by a video endoscope system which has an illuminating optical system for illuminating an object under examination, and a light source unit which emits visible light and excitation light for exciting a living tissue of the object to cause fluorescence. The light source unit alternately transmits the visible light and the excitation light to the illuminating optical system so that a period the excitation light is transmitted to the illuminating optical system may be longer than a period the visible light is transmitted to the illuminating optical system. The video endoscope system also has an objective optical system which converges optical components of the light, other than the excitation light, coming from a surface of the object to form an image of the object, and an image pickup device which picks up the image of the object formed by the objective optical system to convert the image into a video signal. The video endoscope system also has a processor which generates a reference video signal, based on a video signal obtained by the image pickup device during a period when the visible light is transmitted to the illuminating optical system, and a fluorescence video signal based on a video signal obtained by the image pickup device during a period when the excitation light is transmitted to the illuminating optical system.

With the above arrangement, the period during which the object under examination is irradiated with the excitation light is made longer than the period during which the object is illuminated with the visible light. Therefore, the period during which electric charges attributable to the autofluorescence generated from the object accumulates in the image pickup device such as a CCD is made longer than the period during which electric charges attributable to the visible light accumulates in the image pickup device. Thus, the intensity of the video signal corresponding to the image formed by the fluorescence generated from the object output from the image pickup device rises to a level comparable to that of the video signal corresponding to the image formed from the visible light. Consequently, it is no longer necessary to excessively amplify the signal. Therefore, as the fluorescence video signal is subtracted from the reference video signal, a video signal to be used for diagnosis can be produced without lowering the S/N ratio to clearly show any diseased part.

In the second aspect of the invention, there is provided a video endoscope system which has an illuminating optical system which guides light to an object under examination, and a light source unit which emits visible light and excitation light for exciting a living tissue of the object to cause fluorescence. The light source unit transmits the visible light and excitation light to the illuminating optical system and alternately transmit visible light and excitation light to transmit them to the illuminating optical system. The period when the light source unit transmits the excitation light and the period when the light source unit transmits the visible light are adjustable. The video endoscope system also has an objective optical system which converges the optical components of light other than excitation light coming from the surface of the object to form an image of the object, and an image pickup device which picks up the image of the object formed by the objective optical system to convert it into a video signal. The video endoscope system also has a processor which generates a reference video signal based on a video signal obtained by the image pickup device during a period when the visible light is transmitted to the illuminating optical system, and a fluorescence video signal based on a video signal obtained by the image pickup device during a period when the excitation light is transmitted to the illuminating optical system.

With the above arrangement, the period during which the object under examination is irradiated with the excitation light and the period during which the object is illuminated with the visible light can be changed so that the intensity level of the reference video signal and that of the fluorescence video signal may be appropriately regulated.

The light source unit may include a visible light source for emitting visible light and an excitation light source for emitting excitation light. If such is the case, the light source unit may alternately block excitation light and visible light. Typically, this is done by means of a light blocking member, such as a rotary shutter.

Alternatively, the light source unit may be composed of a single light source for emitting light containing a frequency band of both visible light and excitation light. Then, the light source unit alternately transmits visible light and excitation light to the illuminating optical system by alternately inserting a filter transmitting only visible light and a filter transmitting only excitation light in the optical path of light emitted from the light source.

BRIEF DESCRIPTION OF THE DRAWINGS

The invention will be described below in greater detail with reference to the accompanying drawings, in which:

FIG. 1 is a schematic block diagram showing the structure of the video endoscope system according to the first embodiment of the invention;

FIG. 2 is a schematic block diagram showing the structure of the external unit of the first embodiment;

FIGS. 6A and 6B are timing charts for illumination sequence and processes of image acquirement in the fluorescence observation mode;

DESCRIPTION OF THE PREFERRED EMBODIMENTS

Figure 3A:
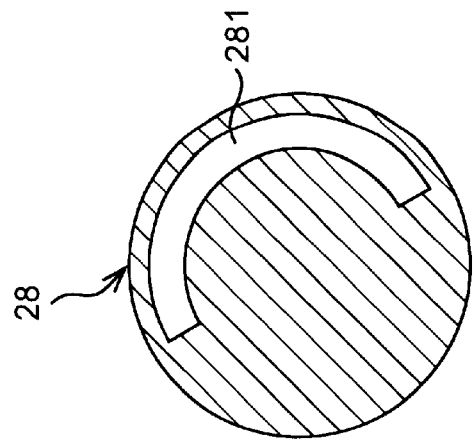
FIGS. 3A, 3B and 3C are front views of a wheel and rotary shutters.

Hereafter, preferred embodiments of a video endoscope system according to the invention will be described with reference to the drawings.

First Embodiment

FIG. 1 is a schematic block diagram showing a structure of a video endoscope system according to a first embodiment of the invention. As shown in FIG. 1, the video endoscope system has a video endoscope 1 and an external unit 2 (including a light source unit and a processor unit).

Although FIG. 1 does not show a concrete structure of the video endoscope 1, it has an insertion section consisting of a flexible tube which is to be inserted into a living body, an operating part integrally coupled to the proximal end of the insertion part, and a light guide flexible tube integrally coupled to the operating part and detachably connected to the external unit 2. A bending mechanism is built into a predetermined area near the distal end of the insertion part. The bending mechanism becomes bent as a dial provided on the operating part is operated. A tip member (not shown) made of a hard material is fixed to the distal end of the insertion part, which is formed with at least three through holes. At a distal end of one of the through holes, a light distribution lens 11 is hermetically provided, at a distal end of another one, an objective lens 12 is hermetically provided and the remainder is used as a forceps hole. The operating part is additionally provided with various operation switches to be used for operating the video endoscope 1. The video endoscope 1 is additionally incorporated with a light guide fiber bundle 13 (which is abbreviated to a "light guide", hereafter) composed of a number of optical fibers. The light guide 13 is led through the insertion part, the operating part and the light guide flexible tube, with its distal end face confronting the light distribution lens 11, and with its proximal end face is inserted into the external unit 2. The light guide 13 and the light distribution lens 11 function as to an illuminating optical system. The video endoscope 1 further includes a CCD (charge-coupled device) area sensor 14 that functions as an image pickup device. The CCD area sensor 14 (which is abbreviated to a CCD, hereafter) has an image pickup plane arranged at the position where the objective lens 12 forms an image of the object under examination when the distal end of the insertion part faces the object. An excitation light cut filter (not shown) is disposed in the optical path between the objective lens 12 and the CCD 14. The excitation light cut filter blocks excitation light for exciting a living body to cause autofluorescence, but transmits visible light. The objective lens 12 and the excitation light cut filter 14 function as an objective optical system. In FIG. 1, two of a plurality of operation switches provided on the operating section of the video endoscope 1 are denoted by 15 and 16. The first operation switch 15 is used to switch between the ordinary observation mode and the fluorescence observation mode. The second operation switch 16 is used for level regulations which will be discussed hereafter.

The external unit 2 is composed of a light source unit 20 and a processor T as shown in FIG. 2.

The light source unit 20 of the external unit 2 includes a white light source 21 and an excitation light source 22. The white light source 21 consists of a xenon lamp and a reflector (not shown). The white light source 21 emits white light generated by the xenon lamp through reflection by the reflector as a parallel beam. The white light source 21 functions as a visible light source. The excitation light source 22 consists of a UV lamp and a reflector (not shown). The UV lamp of the excitation light source 22 generates excitation light whose frequency band is in the ultraviolet spectrum that excites living tissue to cause autofluorescence. The reflector of the excitation light source 22 reflects the excitation light generated by the UV lamp as parallel beam.

A condenser lens 23 is disposed in the optical path of the white light emitted from the white light source 21. The condenser lens 23 converges incident parallel beam onto the proximal end face of the light guide 13. An RGB wheel 24 is disposed between the condenser lens 23 and the light guide 13. As shown in FIG. 3A, the RGB wheel 24 is a disk formed with three fan-shaped apertures of same profiles at regular intervals along its outer periphery. These fan-shaped apertures are fitted with a B filter 241 for transmitting only blue light, a G filter 242 for transmitting only green light and an R filter 243 for transmitting only red light, respectively. While the filters 241, 242 and 243 shown in FIG. 3A have identical profiles, their lengths along the outer periphery of the RGB wheel 24 may differ from each other. More specifically, the B filter 241, the G filter 242 and the R filter 243 may have respective lengths that are arranged in decreasing order along the outer periphery of the RGB wheel 24. The RGB wheel 24 is joined to a motor 24M. As the RGB wheel 24 is rotated by the motor 24M, the B filter 241, the G filter 242 and the R filter 243 are sequentially and repeatedly inserted into the optical path of the light. The motor 24M is rigidly secured to a stage 24G. The stage 24G is linked to a traveling mechanism 24S, which moves the stage 24G with the motor 24M and the RGB wheel 24 vertically in FIG. 2. Specifically, the traveling mechanism 24S moves the RGB wheel 24 between an insertion position where one of the filters 241, 242 or 243 can be inserted into the optical path and a standby position where it is retracted from the optical path. Note that the RGB wheel 24 is located at the standby position in FIG. 2. The RGB wheel 24 reaches the insertion position by moving upward from the standby position in FIG. 2. The motor 24M and the traveling mechanism 24S joined to the RGB wheel 24 function as a wheel drive mechanism.

Figure 3B:
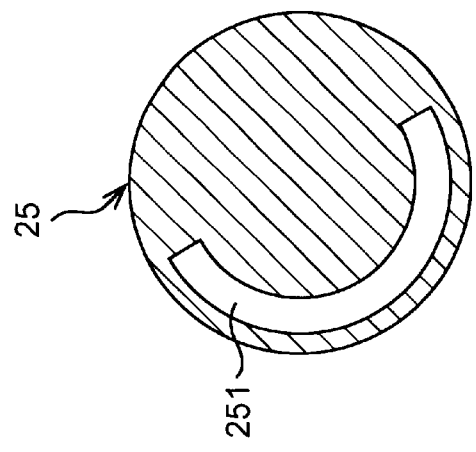
Figure 4A:
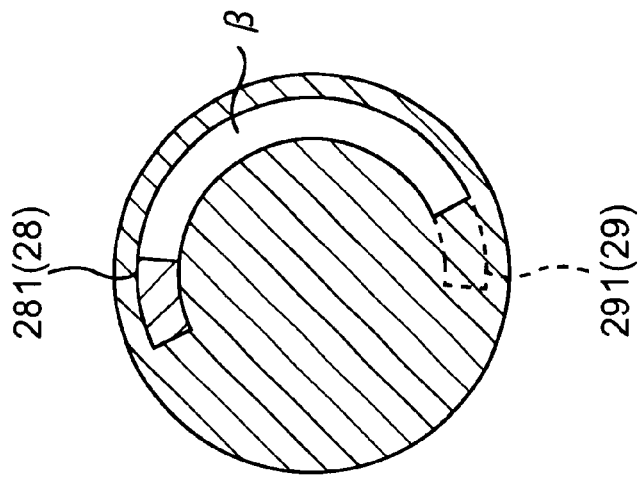
FIGS. 4A and 4B are front views of the rotary shutters showing light transmitting areas.

A pair of rotary shutters 25 and 26 are disposed in front of the white light source 21 in the optical path of the white light emitted from the white light source 21. FIG. 3B shows the first rotary shutter 25. As shown in FIG. 3B, the first rotary shutter 25 is a disk formed with a single arched aperture extending halfway along its outer periphery. A transparent planeparallel plate is fitted into the aperture. The planeparallel plate functions as a transmitting part 251 (a visible light transmitting part) for transmitting the white light. The second rotary shutter 26 has a configuration which is the same as the first rotary shutter 25. The two rotary shutters 25 and 26 are arranged coaxially and in parallel with each other. As shown in FIG. 4A, the transmitting part 251 of the first rotary shutter 25 and the transmitting part 261 of the second rotary shutter 26 partially overlap with each other in a predetermined area. Thus, light is transmitted only through the overlapping area (which is referred to as "transmitting area α", hereafter) of the transmitting parts 251 and 261 with a central angle smaller than the central angle of the individual transmitting parts 251 and 261. As shown in FIG. 2, the rotary shutters 25 and 26 are joined to motors 25M and 26M, respectively. The first rotary shutter 25 is rotated by the motor 25M, while the second rotary shutter 26 is rotated by the motor 26M. The rotary shutters 25 and 26 are arranged such that their drive shafts are parallel with the optical path of the white light emitted from the white light source 21. Note that the first rotary shutter 25 is located in front of the second rotary shutter 26 in the optical path. As the rotary shutters 25 and 26 are rotated at a same rate in synchronism with each other, the transmitting area α is intermittently inserted into the optical path of the white light. The two motors 25M and 26M are rigidly secured to a stage G1. The stage G1 is linked to a traveling mechanism S1, which moves the stage G1 with the motors 25M and 26M vertically in FIG. 2. Specifically, the traveling mechanism S1 moves the stage G1 between an insertion position where the transmitting area α of the rotary shutters 25 and 26 can be inserted into the optical path and a standby position where it is retracted from the optical path. Note that the stage G1 is located at the insertion position in FIG. 2. The stage G1 reaches at the standby position by moving upward from the insertion position in FIG. 2.

The optical path of the white light and that of the excitation light intersect perpendicularly at a predetermined position between the rotary shutter 26 and the condenser lens 23. More specifically, the excitation light source 22 is arranged such that the excitation light emitted therefrom perpendicularly intersects the optical path of the white light emitted from the white light source 21 at the predetermined position. A half mirror 27 is disposed at the intersection of the optical paths of the white light and the excitation light such that it inclines to each of the optical paths at 45°. The half mirror 27 transmits the white light and reflects the excitation light in such a way that the excitation light travels on the same optical path as the white light after passing through itself.

Figure 3C:
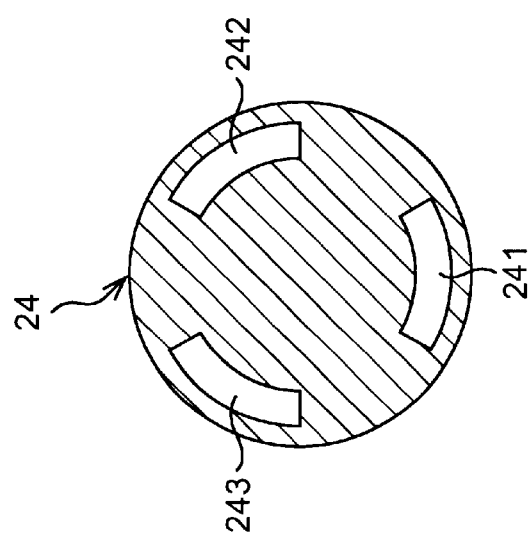
Figure 4B:
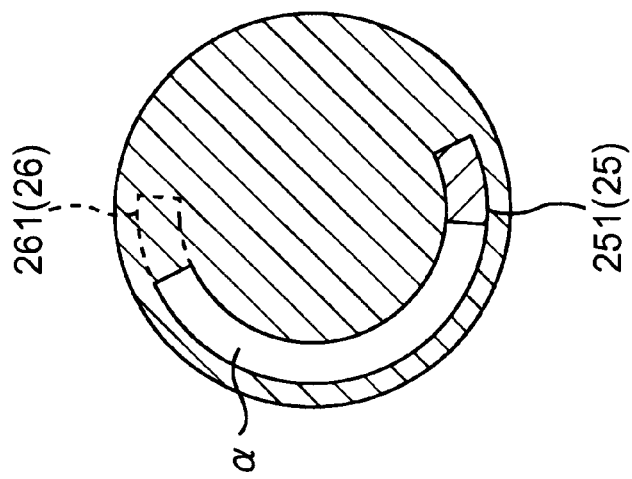

A pair of rotary shutters 28 and 29 are disposed in the optical path of the excitation light between the excitation light source 22 and the half mirror 27. FIG. 3C shows the third rotary shutter 28. The third rotary shutter 28 is a disk formed with a single arched aperture extending halfway along its outer periphery. A transparent planeparallel plate is fitted into the aperture. The planeparallel plate functions as a transmitting part 281 (an excitation light transmitting part) for transmitting the excitation light. The fourth rotary shutter 29 has a configuration which is the same as the third rotary shutter 28. The two rotary shutters 28 and 29 are arranged coaxially and in parallel with each other. As shown in FIG. 4B, the transmitting part 281 of the third rotary shutter 28 and the transmitting part 291 of the fourth rotary shutter 29 partially overlap with each other in a predetermined area. Thus, light is transmitted only through the overlapping area (which is referred to as "transmitting area β", hereafter) of the transmitting parts 281 and 291 with a central angle smaller than the central angle of the individual transmitting parts 281 and 291. As shown in FIG. 2, the rotary shutters 28 and 29 are joined to motors 28M and 29M, respectively.

The third rotary shutter 28 is rotated by the motor 28M, while the fourth rotary shutter 29 is rotated by the motor 29M. The rotary shutters 28 and 29 are arranged such that their drive shafts are parallel with the optical path of the excitation light emitted from the excitation light source 22. Note that the third rotary shutter 28 is located in front of the fourth rotary shutter 29 in the optical path. As the rotary shutters 28 and 29 are rotated at a same rate in synchronous with each other, the transmitting area β is intermittently inserted into the optical path of the excitation light. The half mirror 27 and the two motors 28M and 29M are rigidly secured to a stage G2. The stage G2 is linked to a traveling mechanism S2, which moves the stage G2 vertically in FIG. 2. Specifically, the traveling mechanism S2 moves the stage G2 between an insertion position where the half mirror 27 is put into the optical path of the white light and a standby position where the half mirror 27 is retracted from the optical path of the white light. Note that the stage G2 is located at the insertion position in FIG. 2. The stage G2 reaches the standby position by moving upward from the insertion position in FIG. 2.

The processor T is composed of a timing controller T1, a video signal processing circuit T2 and a system controller T3 that are connected to each other. The timing controller T1 is connected to the motors 24M, 25M, 26M, 28M and 29M through drivers 24D, 25D, 26D, 28D and 29D, respectively.

The timing controller T1 drives the motors 24M, 25M, 26M, 28M and 29M causing them to rotate at a constant rate in synchronism with one another. The control of the drives and the motors 24M, 25M, 26M, 28M and 29M will be described hereafter.

The system controller T3 is connected to the operation switches 15 and 16 of the endoscope 1 and also to the traveling mechanisms 24S, S1 and S2. The system controller T3 can control the RGB wheel 24 to move to the insertion position by controlling the traveling mechanism 24S and, at the same time, control the stages G1 and G2 to move their respective standby positions by controlling the traveling mechanisms S1 and S2, respectively. Under this condition, the light source unit 20 is said to be operating in the ordinary observation mode. On the other hand, as shown in FIG. 2, the system controller T3 can control the RGB wheel 24 to move to a standby position by controlling the traveling mechanism 24S and, at the same time, control the stages G1 and G2 to move to their respective insertion positions by controlling the traveling mechanisms S1 and S2, respectively. Under this condition, the light source unit 20 is said to be operating in a fluorescence observation mode. An operator can use the operation switch 15 to control the system controller T3 to switch the operating mode of the light source unit 20 between the ordinary observation mode and the fluorescence observation mode.

When the light source unit 20 is in the ordinary observation mode, the stage G1 is at the standby position, so that the white light emitted from the white light source 21 enters the condenser lens 23. At the time, the stage G2 is at the standby position, so that the excitation light emitted from the excitation light source 22 does not enter the condenser lens 23. Therefore, as long as the light source unit 20 is in the ordinary observation mode only the white light enters the condenser lens 23. After being transmitted through the condenser lens 23, the white light is sequentially converted into blue light, green light and red light through the respective filters 241, 242 and 243 of the RGB wheel 24. The blue light, green light and red light are then converged on the proximal end face of the light guide 13. Then, the blue light, green light and red light are guided through the light guide 13 to be emitted from its distal end face, and then diverged through the light distribution lens 11. Thus, the light distribution lens 11 emits blue light, green light and red light sequentially and repeatedly. While the object under examination is illuminated sequentially with blue light, green light and red light emitted through the light distribution lens 11, the objective lens 12 of the video endoscope 1 forms images of the object under examination near the image pickup plane of the CCD 14. The CCD 14 converts the images of the object under examination into video signals. As shown in FIG. 1, the CCD 14 is connected to the timing controller T1 of the processor T so that it outputs the video signals in synchronism with the drive signal transmitted from the timing controller T1. The video signal processing circuit T2 of the processor T is connected to the CCD 14 to receive the video signals output from the CCD 14.

Figures 5A, 5B:
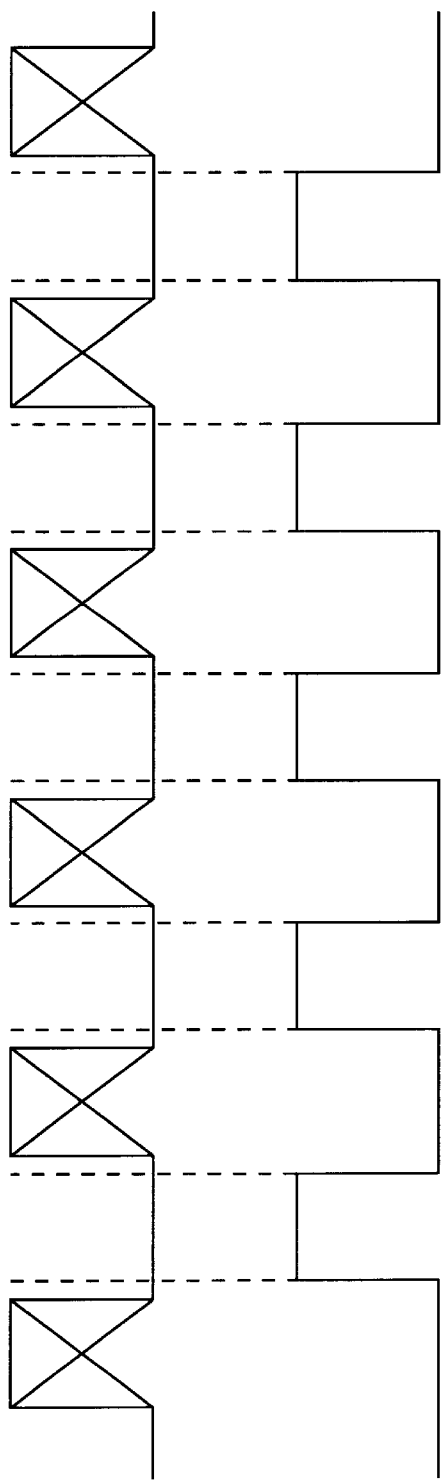
FIGS. 5A and 5B are timing charts for illumination sequence and processes of image acquirement in the ordinary observation mode.

FIGS. 5A and 5B are timing charts for illumination sequence and the processes of image acquirement when the light source unit 20 is set in the ordinary observation mode. FIG. 5A shows the drive signal output from the timing controller T1 to be input to the CCD 14. FIG. 5B shows the irradiation periods during which blue light, green light and red light are emitted through the light distribution lens 11, respectively. As seen from FIGS. 5A and 5B, a "B irradiation" period during which blue light is emitted through the light distribution lens 11 corresponds to a "B accumulation" period for the CCD 14, which means that an electric charge corresponding to the image of the object under examination formed from the blue light is accumulated in each pixel of the CCD 14 when the object under examination is irradiated with blue light. The electric charge accumulated in the "B accumulation" period is transmitted to the video signal processing circuit T2 as a B video signal in a "B transfer" period that comes immediately after "B accumulation" period. The "G accumulation" period that comes immediately after the "B transfer" period corresponds to a "G irradiation" period during which green light is emitted through the light distribution lens 11, which means that an electric charge corresponding to the image of the object under examination formed from the green light is accumulated in each pixel of the CCD 14 during the "G accumulation" period. The electric charge accumulated in the "G accumulation" period is transmitted to the video signal processing circuit T2 as a G video signal in a "G transfer" period that comes immediately after the "G accumulation" period. The "R accumulation" period that comes immediately after the "G transfer" period corresponds to an "R irradiation" period during which red light is emitted through the light distribution lens 11, which means that an electric charge corresponding to the image of the object under examination formed from the red light is accumulated in each pixel of the CCD 14 during the "R accumulation" period. The electric charge accumulated in the "R accumulation" period is transmitted to the video signal processing circuit T2 as an R video signal in an "R transfer" period that comes immediately after the "R accumulation" period. As will be described hereafter, the video signal processing circuit T2 generates a color video signal representing a color image of the object under examination based on the B video signal, the G video signal and the R video signal. As shown in FIG. 1, the video signal processing circuit T2 is connected to a monitor 3 to cause the monitor 3 to display the color image of the object under examination according to the color video signal.

On the other hand, if the light source unit 20 is operating in the fluorescence observation mode as shown in FIG. 2, the white light emitted from the white light source 21 is incident on the half mirror 27 only when the transmission area α of the first and second rotary shutters 25 and 26 is inserted into the optical path of the white light, and the excitation light emitted from the excitation light source 22 is incident on the half mirror 27 only when the transmission area β of the third and fourth rotary shutters 28 and 29 is inserted into the optical path of the excitation light. The timing controller T1 drives the motors 25M, 26M, 28M and 29M at a constant rate in synchronism with one another such that the transmission area β is inserted into the optical path of the excitation light while the transmission area α is retracted from the optical path of the white light, and such that the transmission area α is inserted in the optical path of the white light while the transmission area β is retracted from the optical path of the excitation light. As a result, the white light and the excitation light enter the half mirror 27 alternately and repeatedly. The white light transmitted through the half mirror 27 and the excitation light reflected by the half mirror 27 are then converged on the proximal end face of the light guide 13 through the condenser lens 23. Then, the white light and the excitation light are guided alternately through the light guide 13 to be emitted from its distal end face, and then diverged through the light distribution lens 11. Thus, the white light and the excitation light are emitted through the light distribution lens 11 alternately and repeatedly. In each period during which the object under examination is irradiated with the white light, the light reflected by the surface of the object is focused through the objective lens 12 to form an image of the object near the image pickup plane of the CCD 14. The CCD 14 then converts the image into a video signal. On the other hand, in each period during which the object under examination is irradiated with the excitation light, the object under examination generates autofluorescence. As a result, the autofluorescence generated by the object under examination and the excitation light reflected by the surface of the object enter the objective lens 12. However, since the excitation light is blocked by an excitation light cut filter (not shown), images of the object formed only from the autofluorescence are focused near the image pickup plane of the CCD 14. The CCD 14 outputs video signals according to the drive signal transmitted from the timing controller T1. The video signal processing circuit T2 receives the video signals output from the CCD 14.

FIGS. 6A and 6B are timing charts for illumination sequence and the processes of image acquirement when the light source unit 20 is set in the fluorescence observation mode. FIG. 6A shows the drive signal output from the timing controller T1 to be input to the CCD 14. FIG. 6B shows the irradiation periods during which the excitation light (that is, ultra violet light) and the white light are emitted through the light distribution lens 11, respectively. As seen from FIGS. 6A and 6B, a "W irradiation" period during which the white light is emitted through the light distribution lens 11 corresponds to a "W accumulation" period for the CCD 14, which means that an electric charge corresponding to the image of the object formed from the white light is accumulated in each pixel of the CCD 14 when the object under examination is irradiated with the white light. The electric charge accumulated in the "W accumulation" period is transmitted to the video signal processing circuit T2 as a W video signal (reference video signal) in a "W transfer" period that comes immediately after the "W accumulation" period. A "UV irradiation" period during which the excitation light (ultra violet light) is emitted through the light distribution lens 11 corresponds to an "F accumulation" period of the CCD 14, which means that an electric charge corresponding to the image of the object under examination formed from the autofluorescence is accumulated in each pixel of the CCD 14 when the object is irradiated with the excitation light. The electric charge accumulated in the "F accumulation" period is transmitted to the video signal processing circuit T2 as an F video signal (fluorescence video signal) in an ° F. transfer" period that comes immediately after the "F accumulation" period. The video signal processing circuit T2 generates a diagnostic video signal based on the F video signal and the W video signal. Then, the video signal processing circuit T2 causes the monitor 3 to display a diagnostic image of the object under examination, based on the diagnostic video signal.

Now, the processing in the video signal processing circuit T2 will be described, with reference to FIG. 7. The video signal processing circuit T2 is composed of a pre-processing circuit T21, an A/D converter T22, three memories T23, T24 and T25, and three D/A converters T26, T27 and T28, all of which are connected to the timing controller T1. The pre-processing circuit T21 is connected to the CCD 14. The pre-processing circuit T21 receives the video signal output from the CCD 14 and performs a pre-processing operation, such as amplification and γ correction on the signal. The A/D converter T22 performs an analog-to-digital conversion on the video signal output from the pre-processing circuit T21 and outputs it as digital video data. Each of the three memories T23, T24 and T25 has a storage area capable of storing data of a predetermined number of bits respectively originating from all pixels of the CCD 14. The memories T23, T24 and T25 are connected to the A/D converter T22. Each of the memories T23, T24 and T25 stores the video data output from the A/D converter T22 in each period designated by the timing controller T1. The three D/A converters T26, T27 and T28 are connected to the respective memories T23, T24 and T25. The first D/A converter T26 converts the video data output from the first memory T23 into an analog video signal. The second D/A converter T27 converts the video data output form the second memory T24 into an analog video signal. The third D/A converter T28 converts the video data output from the third memory T25 into an analog video signal. The video signal processing circuit T2 additionally includes a pair of switches SW1 and SW2 respectively connected to the system controller T3. The system controller T3 operates the switches SW1 and SW2 so that the video signals output from the D/A converters T26, T27 and T28 are transmitted to output terminals P1, P2 and P3. The output terminals P1, P2 and P3 are connected to the monitor 3, which is provided with a B component input terminal, a G component input terminal and an R component input terminal for color images. More specifically, the first, second and third output terminals P1, P2 and P3 of the video signal processing circuit T2 are connected to the B component input terminal, the G component input terminal and the R component input terminal, respectively. While not shown, the video signal processing circuit T2 additionally includes another output terminal for outputting a synchronizing signal to be used for displaying a moving image according to a predetermined format. The monitor 3 also includes another input terminal (not shown) for receiving the synchronizing signal, which is connected to the video signal processing circuit T2 for transmitting a synchronizing signal. Thus, the monitor 3 displays a moving color image on its screen based on the video signals and the synchronizing signal received through the input terminals.

The first switch SW1 is used to select a video signal to be transmitted to the first output terminal P1. More specifically, the first switch SW1 selects the video signal from the first D/A converter T26 to transmit it to the first output terminal P1 when the video signal processing circuit T2 is in the ordinary observation mode, and selects the difference between the video signal from the second D/A converter T27 and the video signal from the first D/A converter T26 to transmit it to the first output terminal P1 when the video signal processing circuit T2 is in the fluorescence observation mode. Note that, in FIG. 7, it is in the ordinary observation mode. The second switch SW2 is used to select a video signal to be transmitted to the third output terminal P3. More specifically, the second switch SW2 selects the video signal from the third D/A converter T28 to transmit it to the third output terminal P3 when the video signal processing circuit T2 is in the ordinary observation mode, and selects the video signal from the second D/A converter T27 when the video signal processing circuit T2 is in the fluorescence observation mode. On the other hand, the video signal from the second D/A converter T27 is always transmitted to the second output terminal P2.

Figure 7:
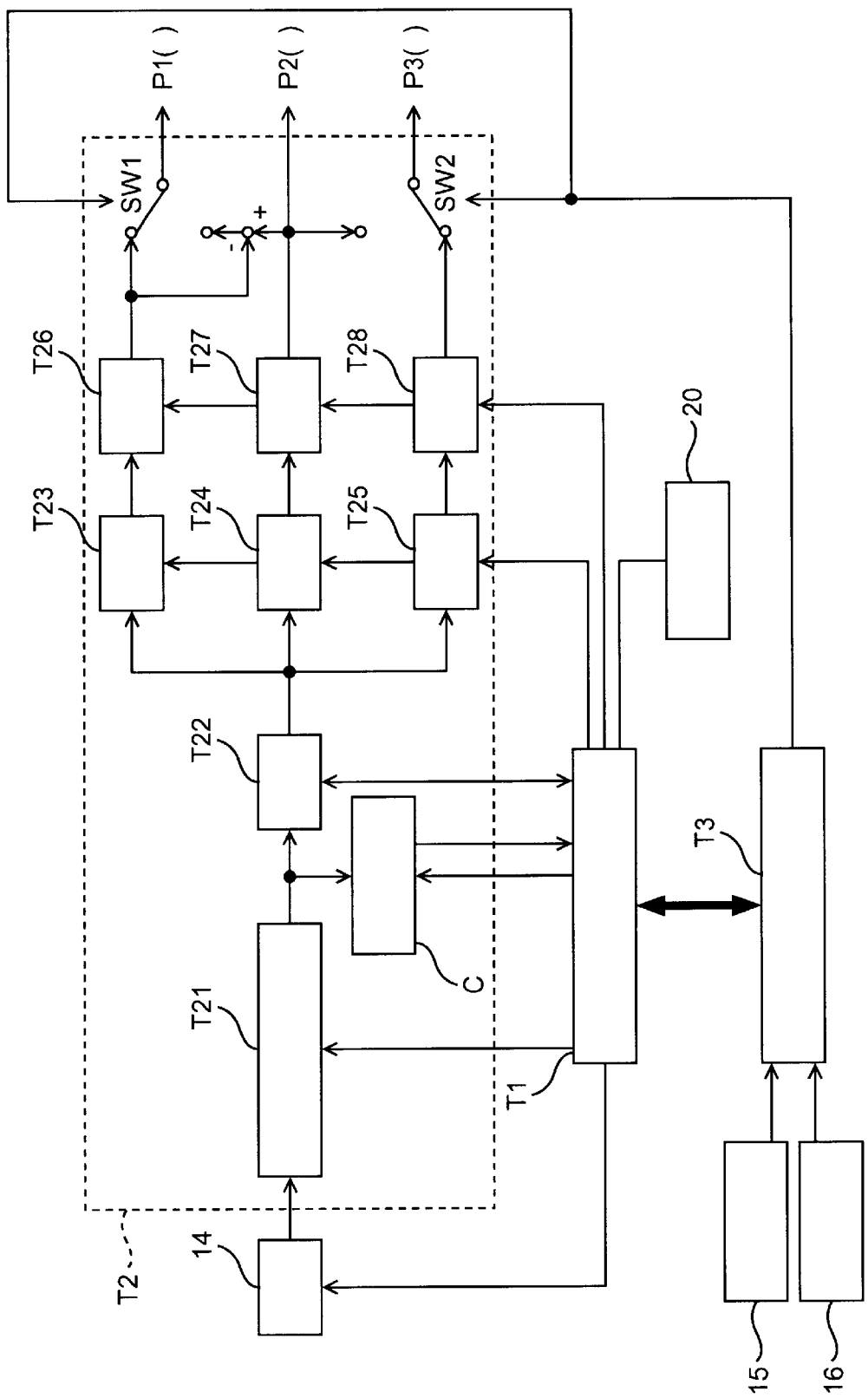
FIG. 7 is a schematic block diagram of the video signal processing circuit.
Figure 8:
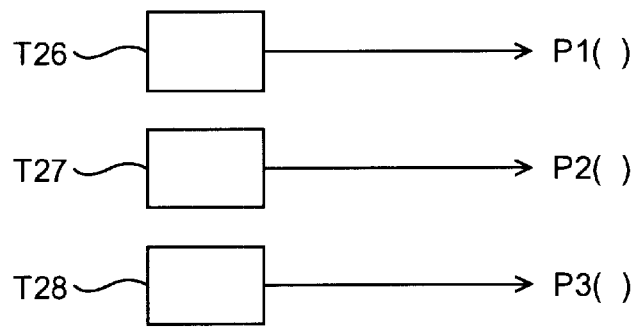
FIG. 8 is an explanatory illustration of the video signal transmission in the ordinary observation mode.

The system controller T3 has ordinary video signals indicating color images of the object under examination transmitted to the monitor 3 by setting the light source unit 20 and the video signal processing circuit T2 (that is, condition of the switches SW1 and SW2 as shown in FIG. 7) to be in the ordinary observation mode, in accordance with operation to the operation switch 15 by the operator. FIG. 8 is a schematic illustration of the video signal transmission in the ordinary observation mode. In this mode, a B video signal, a G video signal and an R video signal are sequentially and repeatedly output from the CCD 14. These video signals are converted into B video data, G video data and R video data, respectively, as they are processed by the pre-processing circuit T21 and the A/D converter T22. Therefore, the A/D converter T22 sequentially outputs the B video data, the G video data and the R video data. During the period in which the A/D converter T22 outputs the B video data, the B video data is stored in the first memory T23. Then, during the period in which the A/D converter T22 outputs the G video data, the G video data is stored in the second memory T24. Finally, during the period in which the A/D converter T22 outputs the R video data, the R video data is stored in the third memory T25. The B video data, the G video data and the R video data are then read out from the memories T23, T24 and T25 respectively at predetermined timing, and subjected to digital-to-analog conversion by the D/A converters T26, T27 and T28, respectively. Since the switches SW1 and SW2 are operated so as to be in the ordinary observation mode in this time, the B video signal, the G video signal and the R video signal respectively output from the D/A converters T26, T27 and T28 are transmitted to the respective output terminals P1, P2 and P3. Then, the B video signal, the G video signal and the R video signal are transmitted to the monitor 3 along with a synchronizing signal, as ordinary image signals. As a result, the monitor 3 displays a moving color image of the object under examination.

Figure 9:
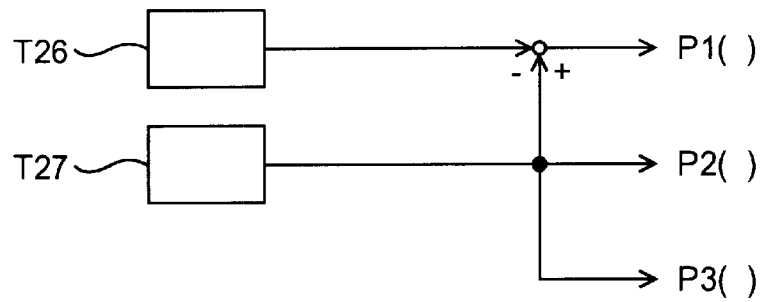
FIG. 9 is an explanatory illustration of the video signal transmission in the fluorescence observation mode.

On the other hand, the system controller T3 has diagnostic video signals generated from the W video signal and the F video signal of the object under examination transmitted to the monitor 3 by setting the light source unit 20 and the video signal processing circuit T2 (especially, condition of switching the switches SW1 and SW2 to the states not shown in FIG. 7) to be in the fluorescence observation mode, in accordance with operation to the operation switch 15 by the operator. FIG. 9 is a schematic illustration of the video signal transmission in the fluorescence observation mode. In this mode, a W video signal and an F video signal are alternately and repeatedly output from the CCD 14. These video signals are converted into W video data and F video data, respectively, as they are processed by the pre-processing circuit T21 and the A/D converter T22. Therefore, the A/D converter T22 alternately outputs the W video data and the F video data. During the period in which the A/D converter T22 outputs the W video data, the W video data is stored in the second memory T24. Then, during the period in which the A/D converter T22 outputs the F video data, the F video data is stored in the first memory T23. In this mode, the third memory T25 is not used. The W video data and the F video data are then read out from the memories T24 and T23 respectively at predetermined timing, and subjected to digital-to-analog conversion by the D/A converters T27 and T26, respectively. Since the switches SW1 and SW2 are operated so as to be in the fluorescence observation mode in this time, to the second output terminal P2 and the third output terminal P3 is transmitted the W video signal which is output from the D/A converter T27 as it is, and to the first output terminal P1 is transmitted the video signal obtained by subtracting the F video signal which is output from the D/A converter T26 from the W video signal, as shown in FIG. 9. The video signals output from the output terminals P1, P2 and P3 are transmitted to the monitor 3 along with a synchronizing signal as diagnostic image signals. As a result, the monitor 3 displays a moving diagnostic image of the object under examination for the purpose of diagnosis.

If only the W video data were transmitted to the output terminals P1, P2 and P3, a monochromatic image of the object under examination that is irradiated with white light would be displayed on the screen of the monitor 3. However, in reality, the video signal obtained by subtracting the F video signal from the W video signal is transmitted to the first output terminal P1 as described above. Therefore, in the diagnostic image displayed on the monitor 3, a part of the object that are not generating autofluorescence is indicated as the monochromatic image. On the other hand, in the image displayed on the monitor 3, the part of the object that are generating autofluorescence are colored in accordance with the intensity of the autofluorescence. Thus, the doctor can recognize the profile of the object under examination and also the intensity distribution of the autofluorescence of the object by observing the diagnostic image displayed on the monitor. Specifically, the doctor can discriminate normal areas where the autofluorescence is intense and diseased areas where the autofluorescence is weak.

The autofluorescence generated from a living body is very weak. Therefore, for appropriately synthesis of diagnostic video signal, it is necessary to regulate the intensity level of the F video signal generated based on the autofluorescence so as to be substantially equal to that of the W video signal, which is called the level regulation. Thus, the timing controller T1 adjusts the "W irradiation" period and the "UV irradiation" period, shown in FIGS. 6A and 6B, so that the intensity of the W video signal may be equal to that of the F video signal by changing the circumferential length of the transmission area α of the first and second rotary shutters 25 and 26, and that of the transmission area β of the third and fourth rotary shutters 28 and 29.

Figure 10:
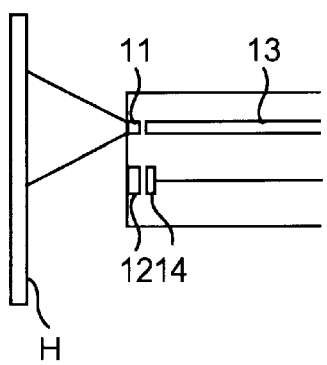
FIG. 10 is a schematic illustration of the usage of a chart.
Figure 11:
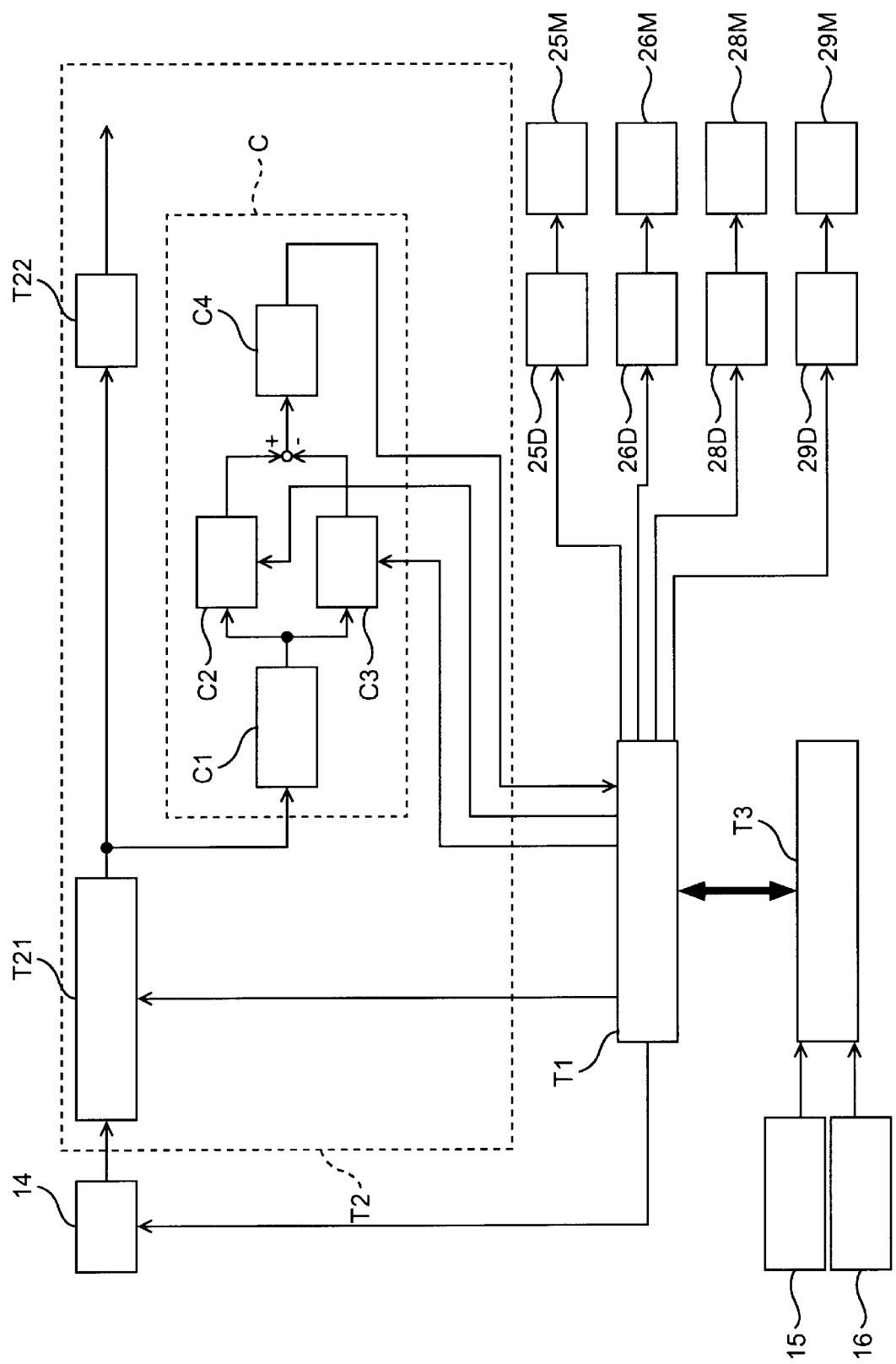
FIG. 11 is a schematic block diagram of the comparator circuit.

The level regulation is conducted with the distal end face of the video endoscope 1 confronting a chart H as shown in FIG. 10, prior to observation for the object under examination. The chart H is a flat panel with fluorescent paint applied to its front surface. The intensity of light reflected by the chart H when irradiated with the white light of a predetermined intensity, and that of the fluorescence generated from the front surface of the chart H when irradiated with the excitation light of a predetermined intensity are preset so that they are equal to those of the object under examination. The operator operates the operation switch 15 to set the light source unit 20 and the video signal processing circuit T2 (especially, the switches SW1 and SW2) to be in the fluorescence observation mode, with the distal end face of the insertion part of the video endoscope 1 confronting the chart H. Subsequently, the operator operates the operation switch 16 to cause the system controller T3 to execute the level regulation. Then, the system controller T3 commands the timing controller T1 to execute the level regulation. Then, the timing controller T1 causes a comparator circuit C1 to firstly compares the intensity of the W image signal and that of the F image signal to obtain a difference between the W image signal and the F image signal. As shown in FIG. 11, the comparator circuit C is composed of an integration circuit C1, a pair of sample hold circuits C2 and C3, a subtractor circuit, and an A/D converter C4. The integration circuit C1 is connected to the pre-processing circuit T21, integrates the signals output from the pre-processing circuit T21 corresponding to all the pixels of the CCD 14, and outputs an integral signals as result of the integration. The sample hold circuits C2 and C3 are connected to the integration circuit C1 and the timing controller T1. The sample hold circuits C2 and C3 hold the respective signals output from the integration circuit C1 for the respective periods specified by the timing controller T1. During the period in which the pre-processing circuit T21 outputs W video signals, the W video signals are integrated in the integration circuit C1. The integral signal (W integral signal) as a result of the integration for the W video signals is then held by the first sample hold circuit C2. During the period in which the pre-processing circuit T21 outputs F video signals, the F video signals are integrated in the integration circuit C1. The integral signal (F integral signal) as a result of the integration for the F video signals is then held by the second sample hold circuit C3. Then, the difference between the W integral signal output from the first sample hold circuit C2 and the F integral signal output from the second sample hold circuit C3 is transmitted to the A/D converter C4. The A/D converter C4 is connected to the timing controller T1 and performs analog-to-digital conversion on the difference signal as the result of the subtraction, and transmits the converted difference signal to the timing controller T1 as judgment data. If the judgment data is equal to 0, the timing controller T1 determines that the intensity of the W accumulation signal and that of the F accumulation signal are at the same level. If, on the other hand, the judgment data is not equal to 0, the timing controller T1 determines that the intensity of the W accumulation signal and that of the F accumulation signal are not at the same level.

As shown in FIG. 11, the timing controller T1 is connected to four drivers 25D, 26D, 28D and 29D. The first driver 25D is connected to the motor 25M and supplies it with a drive current. The second driver 26D is connected to the motor 26M and supplies it with a drive current. The third driver 28D is connected to the motor 28M and supplies it with a drive current. The fourth driver 29D is connected to the motor 29M and supplies it with a drive current. The motors 25D, 26D, 28D and 29D, and the driver 25M, 26M, 28M and 29M function as a shutter drive mechanism. The timing controller T1 can adjust the peripheral length of the transmission area α shown in FIG. 4A and hence the "w irradiation" period shown in FIG. 6B, by controlling the drivers 25D and 26D so that the phase difference between the motors 25M and 26M and hence the phase difference between the rotary shutters 25 and 26 are adjusted. Similarly, the timing controller T1 can adjust the peripheral length of the transmission area β, shown in FIG. 4B and hence the "UV irradiation" period shown in FIG. 6B, by controlling the drivers 28D and 29D so that the phase difference between the motor, 28M and 29M and hence the phase difference between the rotary shutters 28 and 29 are adjusted.

Figures 12A, 12B:
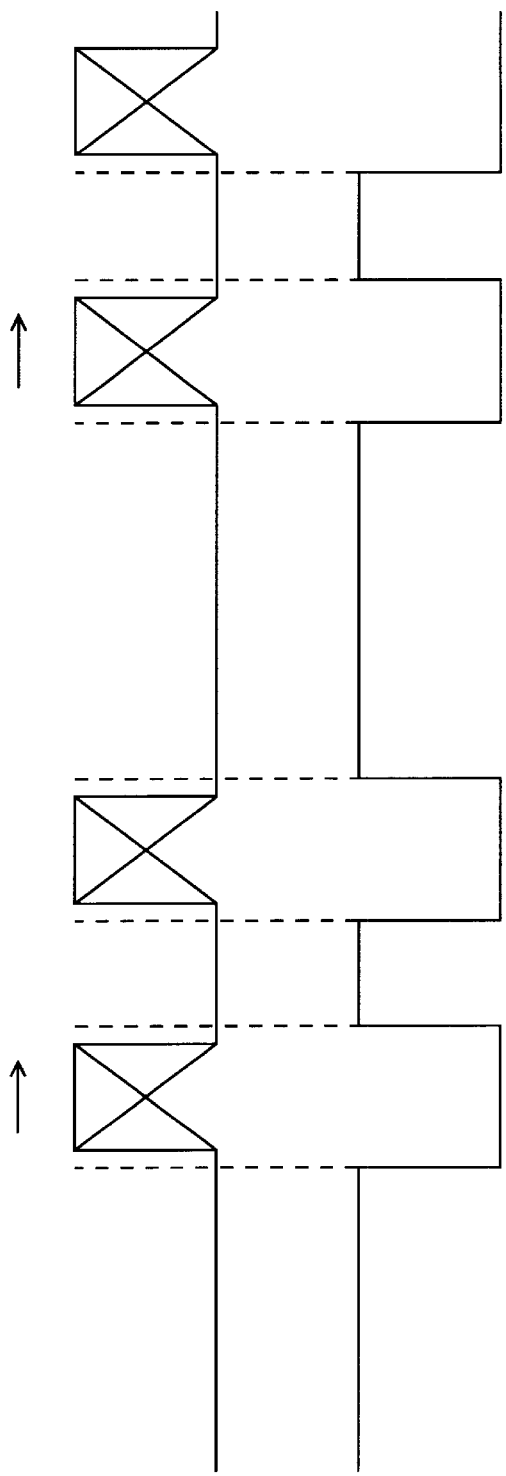
FIGS. 12A and 12B are timing charts showing a state after a level regulation.
Figures 13A, 13B:
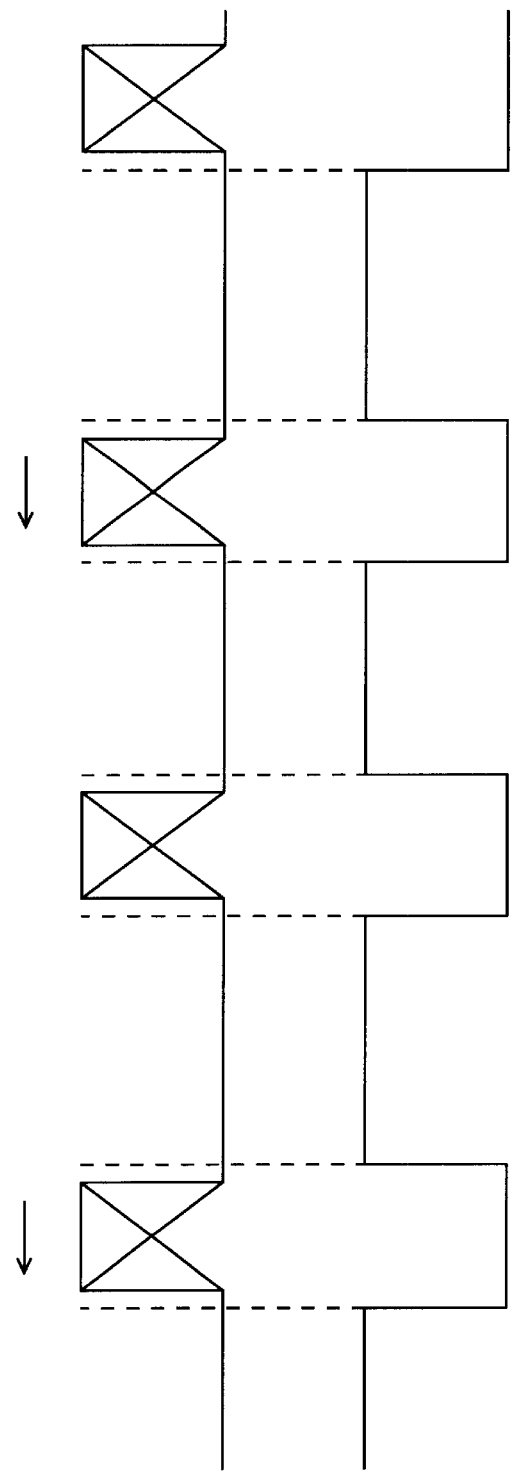
FIGS. 13A and 13B is another timing chart showing a state after a level regulation.

When the judgment data output from the comparator circuit C is positive, the timing controller T1 determines that the W accumulation signal is greater than the F accumulation signal. Then, the timing controller T1 delays the timing of the start of the "F transfer" period from the one shown in FIG. 6A. Specifically, the timing controller T1 shifts the "F transfer" period to the right in FIG. 6A. At the same time, the timing controller T1 terminates the "UV irradiation" period immediately before the start of the "F transfer" period and starts the "W irradiation" period immediately after the end of the "F transfer" period. As a result, the "UV irradiation" period is extended and the "W irradiation" period is shortened so that the "F accumulation" period is extended and the "W accumulation" period is shortened as shown in FIGS. 12A and 12B. The judgment data is consequently reduced. When the judgment data is made equal to 0, the timing controller T1 fixes the timing of the start of the "F transfer" period and the phases of the motors 25M, 26M, 28M and 29M. When, on the other hand, the judgment data output from the comparator circuit C is negative, the timing controller T1 determines that the F accumulation signal is greater than the W accumulation signal. Then, the timing controller T1 advances the timing of the start of the "F transfer" period from the one shown in FIG. 6A. In other words, the timing controller T1 shifts the "F transfer" period to the left in FIG. 6A. At the same time, the timing controller T1 terminates the "UV irradiation" period immediately before the start of the "F transfer" period and starts the "W irradiation" period immediately after the end of the "F transfer" period. As a result, the "UV irradiation" period is shortened and the "W irradiation" period is extended so that the "F accumulation" period is shortened and the "W accumulation" period is extended as shown in FIGS. 13A and 13B. The judgment data is consequently increased. When the judgment data is made equal to 0, the timing controller T1 fixes the timing of the start of the "F transfer" period and the phases of the motors 25M, 26M, 28M and 29M.

As described above, the operator can perform the level regulation in a simple way by operating the operation switch 16 while holding the distal end face of the video endoscope 1 so as to confront the chart H. After the level regulation, the timing controller T1 holds the timing of the start of the "F transfer" period and the phases of the motors 25M, 26M, 28M, 29M. Therefore, after the level regulation, a diagnostic video signal appropriate to observe the object under examination can be obtained. Note that, in the process of synthesizing a diagnostic image, the level of the F video signal obtained based on the autofluorescence from the living body is regulated by mainly regulating the UV irradiation period. On the other hand, the level of the W video signal is regulated by mainly regulating the W irradiation period. Thus, proper F video signal, proper W video signal and therefore proper diagnostic video signal with a high S/N ratio can be obtained anytime. The diagnostic video signal makes the monitor 3 display a clear diagnostic image that is mostly free from noise. Then, the doctor can accurately diagnose the diseased portion by observing the displayed clear diagnostic image of the object under examination.

It should be noted that the intensity of the autofluorescence generated by healthy tissue can vary from place to place in a living body. Therefore, the chart H is preferably prepared for each part of the living body to be observed. Thus, the operator can perform the level regulation in a simple way each time a part of the living body to be observed is newly selected. It may alternatively be so arranged that the timing controller T1 adjust the "UV irradiation" period and the "W irradiation" period by shifting the timing of the start of the "W transfer" period.

Second Embodiment

Figure 14:
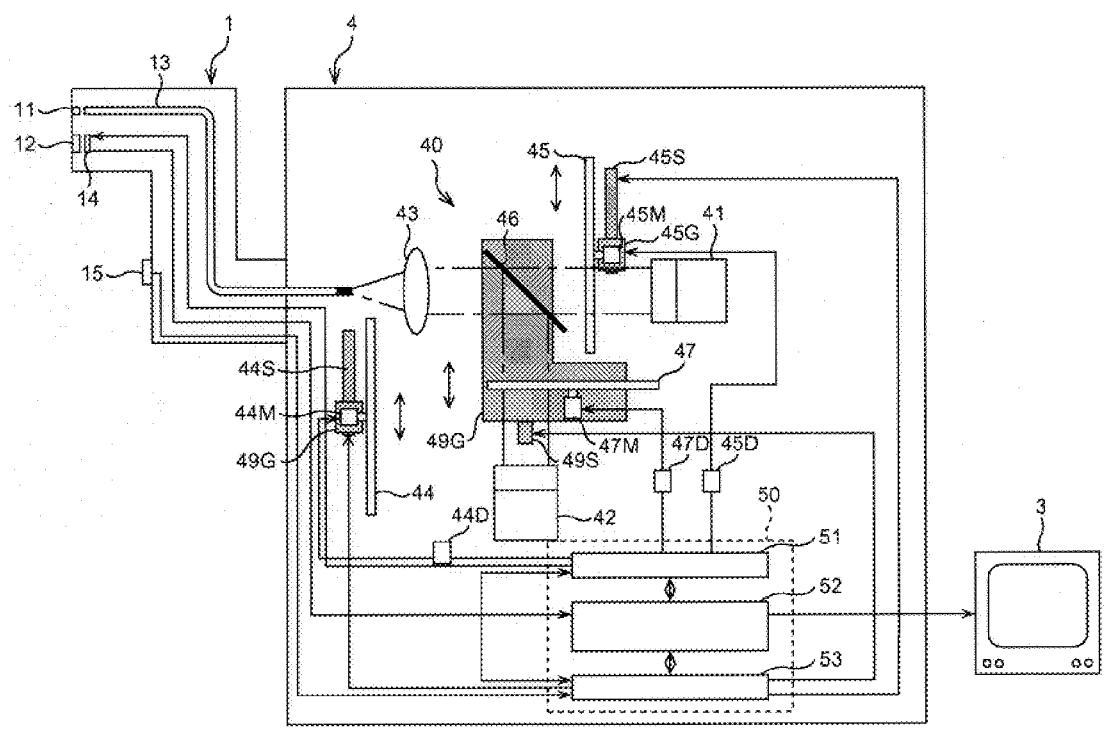
FIG. 14 is a schematic block diagram showing the structure of the video endoscope system according to the second embodiment of the invention.

FIG. 14 is a schematic block diagram showing a structure of a video endoscope system according to a second embodiment of the invention. As shown in FIG. 14, the video endoscope system has a video endoscope 1 and an external unit 4 (including a light source unit and a processor unit). The video endoscope 1 has quite same structure as the first embodiment. The external unit 4 is composed of a light source unit 40 and a processor 50 as shown in FIG. 14.

The light source unit 40 of the external unit 4 includes a white light source 41 and an excitation light source 42. The white light source 41 consists of a xenon lamp and a reflector (not shown). The white light source 41 emits white light generated by the xenon lamp and then reflected by the reflector as a parallel beam. The white light source 41 functions as a visible light source. The excitation light source 42 consists of a UV lamp and a reflector (not shown). The UV lamp of the excitation light source 42 generates excitation light whose frequency band is in the ultraviolet spectrum that excites living tissue to cause autofluorescence. The reflector of the excitation light source 42 reflects the excitation light generated by the UV lamp as parallel beam.

Figure 15A:
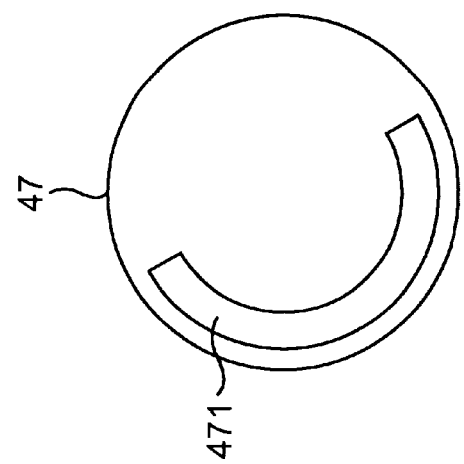
FIGS. 15A, 15B and 15C are front views of a wheel and rotary shutters.

A condenser lens 43 is disposed in the optical path of the white light emitted from the white light source 41. The condenser lens 43 converges incident parallel beam onto the proximal end face of the light guide 13 of the video endoscope 1. An RGB wheel 44 is disposed between the condenser lens 43 and the light guide 13. As shown in FIG. 15A, the RGB wheel 44 is a disk formed with three fan-shaped apertures of same profiles at regular intervals along its outer periphery. These fan-shaped apertures are fitted with a B filter 441 for transmitting only blue light, a G filter 442 for transmitting only green light and an R filter 443 for transmitting only red light, respectively. While the filters 441, 442 and 443 shown in FIG. 15A have identical profiles, their lengths along the outer periphery of the RGB wheel 44 may differ from each other. More specifically, the B filter 441, the G filter 442 and the R filter 443 may have respective lengths that are arranged in decreasing order along the outer periphery of the RGB wheel 44. The RGB wheel 44 is joined to a motor 44M. As the RGB wheel 44 is rotated by the motor 44M, the B filter 441, the G filter 442 and the R filter 443 are sequentially and repeatedly inserted into the optical path of the light. The motor 44M is rigidly secured to a stage 44G. The stage 44G is linked to a traveling mechanism 44S, which moves the stage 44G with the motor 44M and the RGB wheel 44 vertically in FIG. 14. Specifically, the traveling mechanism 44S moves the RGB wheel 44 between an insertion position where one of the filters 441, 442 or 443 can be inserted into the optical path and a standby position where it is retracted from the optical path. Note that the RGB wheel 44 is located at the standby position in FIG. 14. The RGB wheel 44 reaches the insertion position by moving upward from the standby position in FIG. 14. The motor 44M and the traveling mechanism 44S joined to the RGB wheel 44 function as a wheel drive mechanism.

Figure 15B:
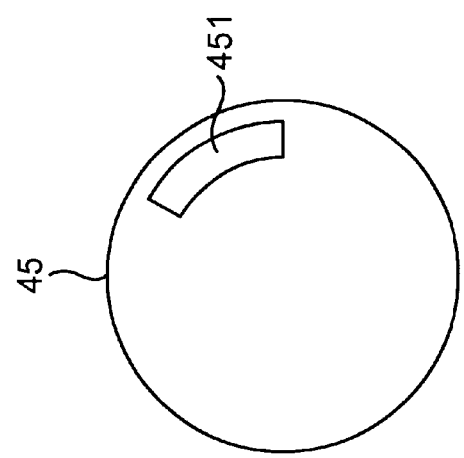

A first rotary shutter 45 is disposed in front of the white light source 41 in the optical path of the white light emitted from the white light source 41. As shown in FIG. 15B, the first rotary shutter 45 is a disk formed with a single arched aperture along its outer periphery. A transparent planeparallel plate is fitted into the aperture. The planeparallel plate functions as a transmitting part 451 (a visible light transmitting part) for transmitting the white light. The shape of the transmitting part 451 is same as each of the G filter 442 of the RGB wheel 44. The first rotary shutter 45 is joined to a motor 45M. As the first rotary shutter 45 is rotated by the motor 45M, the transmitting part 451 is intermittently inserted into the optical path of the white light. The motor 45M is rigidly secured to a stage 45G. The stage 45G is linked to a traveling mechanism 45S, which moves the stage 45G with the motor 45M vertically in FIG. 14. Specifically, the traveling mechanism 45S moves the stage 45G between an insertion position where the transmitting part 451 of the first rotary shutter 45 can be inserted into the optical path and a standby position where it is retracted from the optical path. Note that the stage 45G is located at the insertion position in FIG. 14. The stage 45G reaches at the standby position by moving upward from the insertion position in FIG. 14.

The optical path of the white light and that of the excitation light intersect perpendicularly at a predetermined position between the rotary shutter 45 and the condenser lens 43. More specifically, the excitation light source 42 is arranged such that the excitation light emitted therefrom perpendicularly intersects the optical path of the white light emitted from the white light source 41 at the predetermined position. A half mirror 46 is disposed at the intersection of the optical paths of the white light and the excitation light such that it inclines to each of the optical paths at 45°. The half mirror 46 transmits the white light and reflects the excitation light in such a way that the excitation light travels on the same optical path as the white light after passing through itself.

Figure 15C:
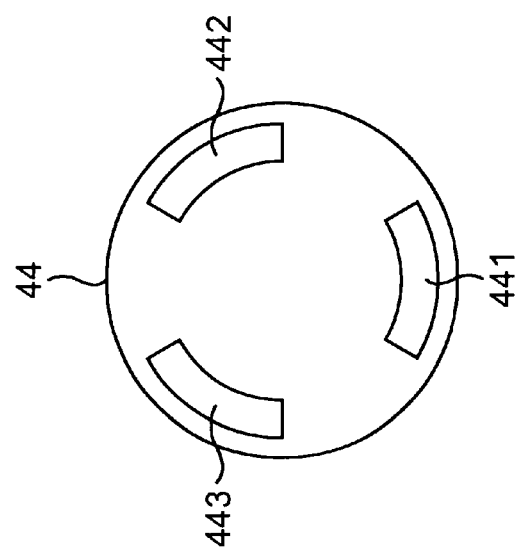

A second rotary shutter 47 is disposed in the optical path of the excitation light between the excitation light source 42 and the half mirror 46. As shown in FIG. 15C, the second rotary shutter 47 is a disk formed with a single arched aperture extending about halfway along its outer periphery. A transparent planeparallel plate is fitted into the aperture. The planeparallel plate functions as a transmitting part 471 (an excitation light transmitting part) for transmitting the excitation light. As shown in FIG. 14, the second rotary shutter 47 is joined to a motors 47M. As the rotary shutter 47 is rotated, the transmitting part 471 is intermittently inserted into the optical path of the excitation light. The half mirror 46 and the motor 47M are rigidly secured to a stage 49G. The stage 49G is linked to a traveling mechanism 49S, which moves the stage 49G vertically in FIG. 14. Specifically, the traveling mechanism 49S moves the stage 49G between an insertion position where the half mirror 46 is put into the optical path of the white light and a standby position where the half mirror 46 is retracted from the optical path of the white light. Note that the stage 49G is located at the insertion position in FIG. 14. The stage 49G reaches the standby position by moving upward from the insertion position in FIG. 14.

The processor 50 is composed of a timing controller 51, a video signal processing circuit 52 and a system controller 53 that are connected to each other. The timing controller 51 is connected to the motors 44M, 45M and 47M through drivers 44D, 45D and 47D, respectively.

The timing controller 51 drives the motors 44M, 45M and 47M causing them to rotate at a constant rate in synchronism with one another.

The system controller 53 is connected to the operation switch 15 of the endoscope 1 and also to the traveling mechanisms 44S, 45S and 49S. The system controller 53 can control the RGB wheel 44 to move to the insertion position by controlling the traveling mechanism 44S and, at the same time, control the stages 45G and 49G to move their respective standby positions by controlling the traveling mechanisms 45S and 49S, respectively. Under this condition, the light source unit 40 is said to be operating in the ordinary observation mode. On the other hand, as shown in FIG. 14, the system controller 53 can control the RGB wheel 44 to move to a standby position by controlling the traveling mechanism 44S and, at the same time, control the stages 45G and 49G to move to their respective insertion positions by controlling the traveling mechanisms 45S and 49S, respectively. Under this condition, the light source unit 40 is said to be operating in a fluorescence observation mode. An operator can use the operation switch 15 to control the system controller 53 to switch the operating mode of the light source unit 40 between the ordinary observation mode and the fluorescence observation mode.

When the light source unit 40 is in the ordinary observation mode, the stage 45G is at the standby position, so that the white light emitted from the white light source 41 enters the condenser lens 43. At the time, the stage 49G is at the standby position, so that the excitation light emitted from the excitation light source 42 does not enter the condenser lens 43. Therefore, as long as the light source unit 40 is in the ordinary observation mode, only the white light enters the condenser lens 43. After being transmitted through the condenser lens 43, the white light is sequentially converted into blue light, green light and red light through the respective filters 441, 442 and 443 of the RGB wheel 44. The blue light, green light and red light are then converged on the proximal end face of the light guide 13. Then, the blue light, green light and red light are guided through the light guide 13 to be emitted from its distal end face, and then diverged through the light distribution lens 11. Thus, the light distribution lens 11 emits blue light, green light and red light sequentially and repeatedly. While the object under examination is illuminated sequentially with blue light, green light and red light emitted through the light distribution lens 11, the objective lens 12 of the video endoscope 1 forms images of the object under examination near the image pickup plane of the CCD 14. The CCD 14 converts the images of the object under examination into video signals. As shown in FIG. 1, the CCD 14 is connected to the timing controller 51 of the processor 50 so that it outputs the video signals in synchronism with the drive signal transmitted from the timing controller 51. The video signal processing circuit 52 of the processor 50 is connected to the CCD 14 to receive the video signals output from the CCD 14. The timing charts of FIGS. 5A and 5B also agree with the illumination sequence and the processes of image acquirement in the second embodiment when the light source unit 40 is set in the ordinary observation mode.

The video signal processing circuit 52 generates a color video signal representing a color image of the object under examination based on the B video signal, the G video signal and the R video signal. As shown in FIG. 14, the video signal processing circuit 52 is connected to a monitor 3 to cause the monitor 3 to display the color image of the object under examination according to the color video signal.

On the other hand, if the light source unit 40 is operating in the fluorescence observation mode as shown in FIG. 14, the white light emitted from the white light source 41 is incident on the half mirror 46 only when the transmitting part 451 of the first rotary shutter 45 is inserted into the optical path of the white light, and the excitation light emitted from the excitation light source 42 is incident on the half mirror 46 only when the transmitting part 471 of the second rotary shutter 47 is inserted into the optical path of the excitation light. The timing controller 51 drives the motors 45M and 49M at a constant rate in synchronism with each other such that the transmitting part 471 is inserted into the optical path of the excitation light while the transmitting part 451 is retracted from the optical path of the white light, and such that the transmitting part 451 is inserted in the optical path of the white light while the transmitting part 471 is retracted from the optical path of the excitation light. As a result, the white light and the excitation light enter the half mirror 46 alternately and repeatedly and the excitation light enter the half mirror 46 longer time than white light, because the length of transmitting part 471 along outer periphery of the second rotary shutter 47 is longer than that of the transmitting part 451 along outer periphery of the first rotary shutter 45 as shown in FIG. 15B and FIG. 15C. The white light transmitted through the half mirror 46 and the excitation light reflected by the half mirror 46 are then converged on the proximal end face of the light guide 13 through the condenser lens 43. Then, the white light and the excitation light are guided alternately through the light guide 13 to be emitted from its distal end face, and then diverged through the light distribution lens 11. Thus, the white light and the excitation light are emitted through the light distribution lens 11 alternately and repeatedly. In each period during which the object under examination is illuminated with the white light, the light reflected by the surface of the object is focused through the objective lens 12 to form an image of the object near the image pickup plane of the CCD 14. The CCD 14 then converts the image into a video signal. On the other hand, in each period during which the object under examination is irradiated with the excitation light, the object under examination generates autofluorescence. As a result, the autofluorescence generated by the object under examination and the excitation light reflected by the surface of the object enter the objective lens 12. However, since the excitation light is blocked by an excitation light cut filter (not shown), images of the object formed only from the autofluorescence near the image pickup plane of the CCD 14. The CCD 14 outputs video signals according to the drive signal transmitted from the timing controller 51. The video signal processing circuit 52 receives the video signals output from the CCD 14. The timing charts of FIGS. 6A and 6B also agree with the illumination sequence and the processes of image acquirement in the second embodiment when the light source unit 40 is set in the fluorescence observation mode.

The video signal processing circuit 52 generates a diagnostic video signal based on the F video signal and the W video signal. Then, the video signal processing circuit 52 causes the monitor 3 to display a diagnostic image of the object under examination, based on the diagnostic video signal.

Now, the processing in the video signal processing circuit 52 will be described, with reference to FIG. 16. The video signal processing circuit 52 is composed of a pre-processing circuit 521, an A/D converter 522, three memories 523, 524 and 525, and three D/A converters 526, 527 and 528, all of which are connected to the timing controller 51. The pre-processing circuit 521 is connected to the CCD 14. The pre-processing circuit 521 receives the video signal output from the CCD 14 and performs a pre-processing operation, such as amplification and y correction on the signal. The A/D converter 522 performs an analog-to-digital conversion on the video signal output from the pre-processing circuit 521 and outputs it as digital video data. Each of the three memories 523, 524 and 525 has a storage area capable of storing data of a predetermined number of bits respectively originating from all pixels of the CCD 14. The memories 523, 524 and 525 are connected to the A/D converter 522. Each of the memories 523, 524 and 525 store the video data output from the A/D converter 522 in each period designated by the timing controller 51. The three D/A converters 526, 527 and 528 are connected to the respective memories 523, 524 and 525. The first D/A converter 526 converts the video data output from the first memory 523 into an analog video signal. The second D/A converter 527 converts the video data output form the second memory 524 into an analog video signal. The third D/A converter 528 converts the video data output from the third memory 525 into an analog video signal. The video signal processing circuit 52 additionally includes a pair of switches SW1 and SW2 respectively connected to the system controller 53. The system controller 53 operates the switches SW1 and SW2 so that the video signals output from the D/A converters 526, 527 and 528 are transmitted to output terminals P1, P2 and P3. The output terminals P1, P2 and P3 are connected to the monitor 3, which has same structure as the first embodiment. More specifically, the first, second and third output terminals P1, P2 and P3 of the video signal processing circuit 52 are connected to the B component input terminal, the G component input terminal and the R component input terminal of the monitor 3, respectively. While not shown, the video signal processing circuit 52 additionally includes another output terminal for outputting a synchronizing signal to be used for displaying a moving image according to a predetermined format, which is connected to an input terminal (not shown) for receiving the synchronizing signal of the monitor 3. Thus, the monitor 3 displays a moving color image on its screen based on the video signals and the synchronizing signal received through the input terminals.

The first switch SW1 is used to select a video signal to be transmitted to the first output terminal P1. More specifically, the first switch SW1 selects the video signal from the first D/A converter 526 to transmit it to the first output terminal P1 when the video signal processing circuit 52 is in the ordinary observation mode, and selects the difference between the video signal from the second D/A converter 527 and the video signal from the first D/A converter 526 to transmit it to the first output terminal P1 when the video signal processing circuit 52 is in the fluorescence observation mode. Note that, in FIG. 16, it is in the ordinary observation mode. The second switch SW2 is used to select a video signal to be transmitted to the third output terminal P3. More specifically, the second switch SW2 selects the video signal from the third D/A converter 528 to transmit it to the third output terminal P3 when the video signal processing circuit 52 is in the ordinary observation mode, and selects the video signal from the second D/A converter 527 when the video signal processing circuit 52 is in the fluorescence observation mode. On the other hand, the video signal from the second D/A converter 527 is always transmitted to the second output terminal P2.

Figure 16:
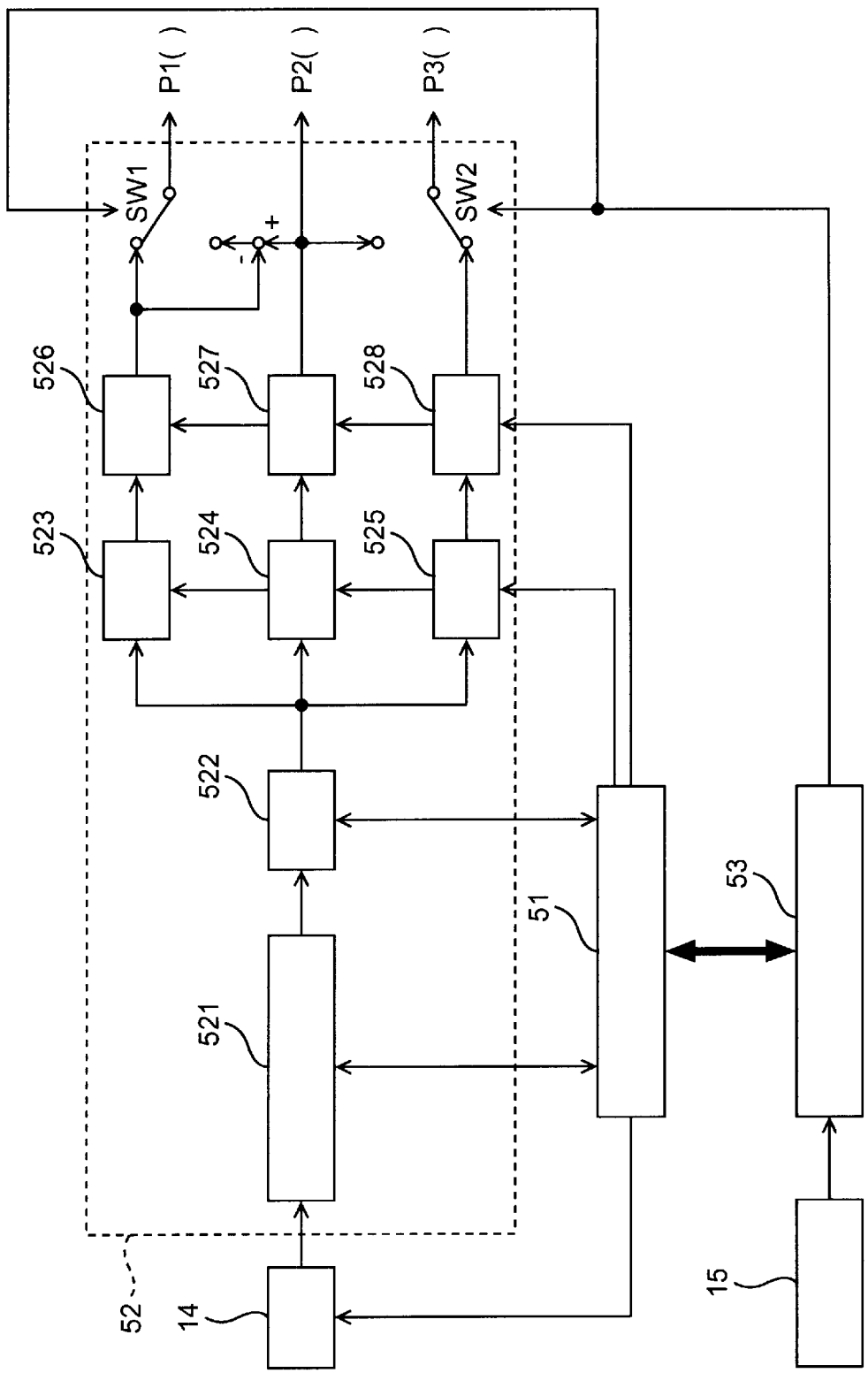
FIG. 16 is a schematic block diagram of the video signal processing circuit.

The system controller 53 has ordinary video signals indicating color images of the object under examination transmitted to the monitor 3 by setting the light source unit 40 and the video signal processing circuit 52 (that is, condition of the switches SW1 and SW2 as shown in FIG. 16) to be in the ordinary observation mode, in accordance with operation to the operation switch 15 by the operator.

Figure 17:
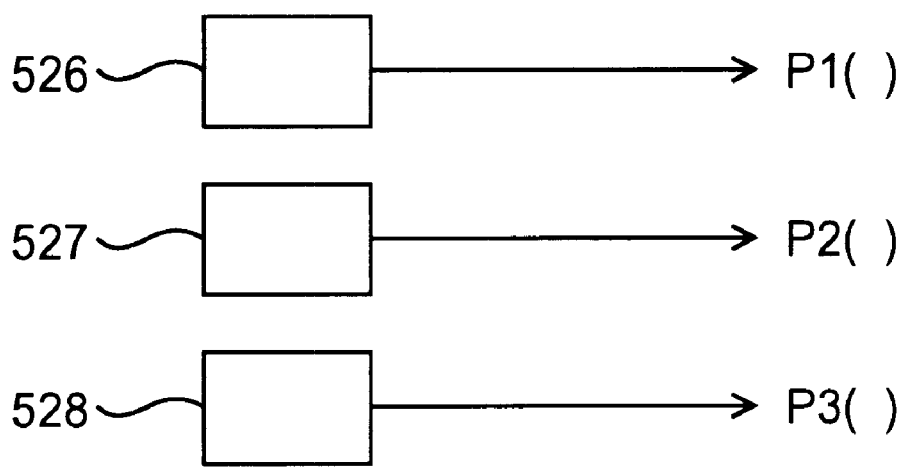
FIG. 17 is an explanatory illustration of the processing in the ordinary observation mode.

FIG. 17 is a schematic illustration of the video signal transmission in the ordinary observation mode. In this mode, a B video signal, a G video signal and an R video signal are sequentially and repeatedly output from the CCD 14. These video signals are converted into B video data, G video data and R video data, respectively, as they are processed by the pre-processing circuit 521 and the A/D converter 522. Therefore, the A/D converter 522 sequentially outputs the B video data, the G video data and the R video data. During the period in which the A/D converter 522 outputs the B video data, the B video data is stored in the first memory 523. Then, during the period in which the A/D converter 522 outputs the G video data, the G video data is stored in the second memory 524. Finally, during the period in which the A/D converter 522 outputs the R video data, the R video data is stored in the third memory 525. The B video data, the G video data and the R video data are then read out from the memories 523, 524 and 525 respectively at predetermined timing, and subjected to digital-to-analog conversion by the D/A converters 526, 527 and 528, respectively. Since the switches SW1 and SW2 are operated so as to be in the ordinary observation mode in this time, the B video signal, the G video signal and the R video signal respectively output from the D/A converters 526, 527 and 528 are transmitted to the respective output terminals P1, P2 and P3. Then, the B video signal, the G video signal and the R video signal are transmitted to the monitor 3 along with a synchronizing signal, as ordinary image signals. As a result, the monitor 3 displays a moving color image of the object under examination.

Figure 18:
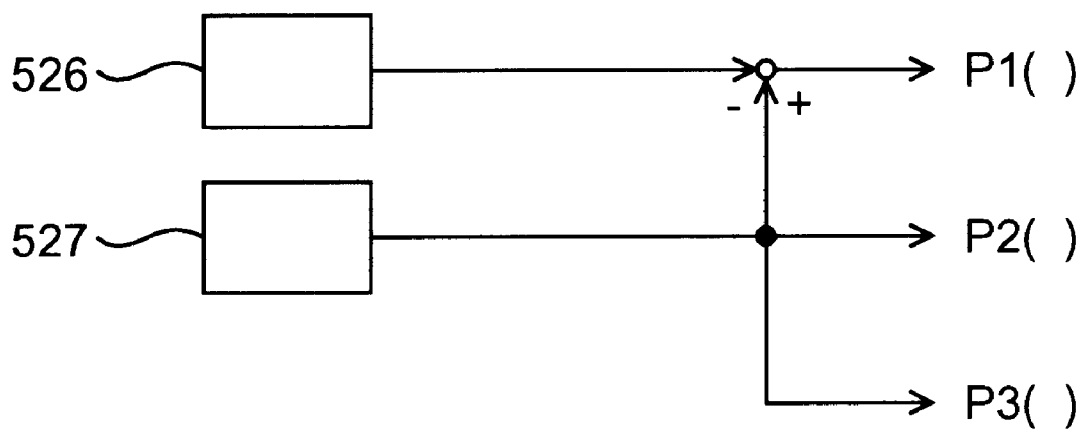
FIG. 18 is an explanatory illustration of the processing in the fluorescence observation mode.
Figure 19A:
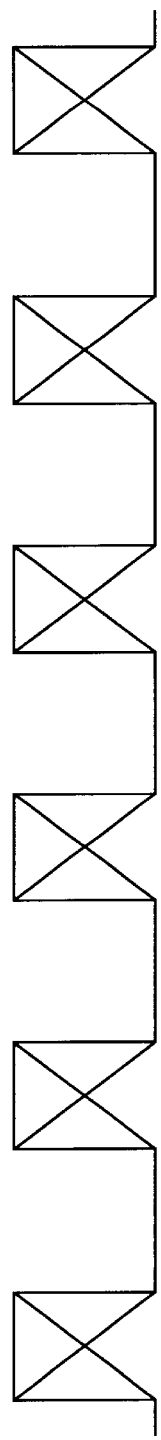
FIGS. 19A, 19B, 19C and 19D are a timing chart for illumination of light and processes of image acquirement in a conventional system.
Figure 19B:
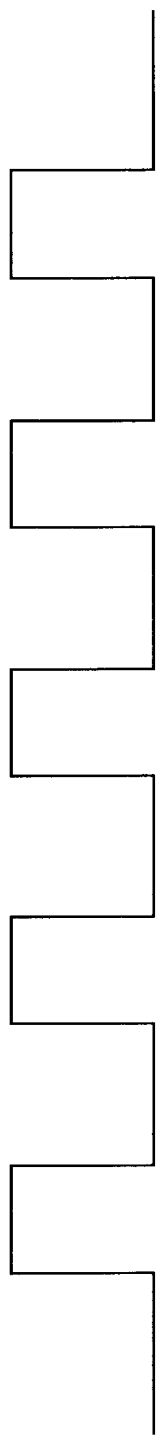
Figure 19C:
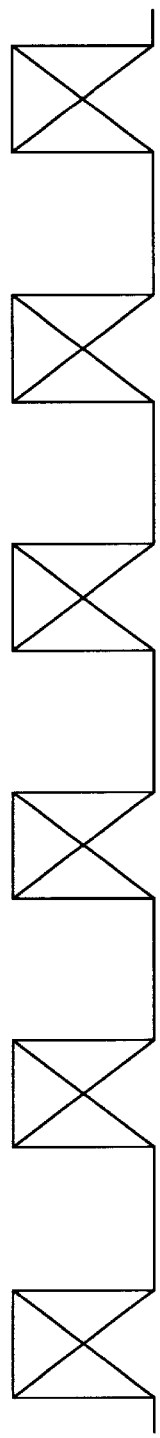
Figure 19D:
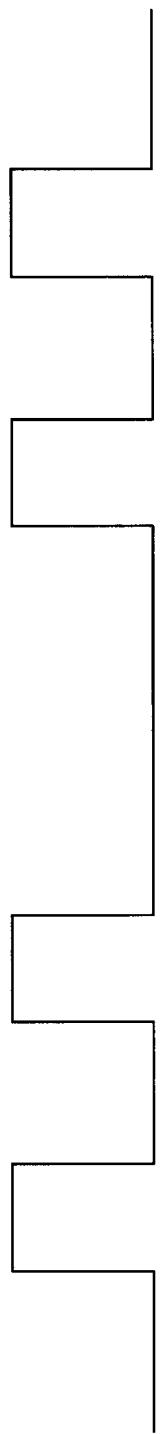

On the other hand, the system controller 53 has diagnostic video signals generated from the W video signal and the F video signal of the object under examination transmitted to the monitor 3 by setting the light source unit 40 and the video signal processing circuit 52 (especially, condition of switching the switches SW1 and SW2 to the states not shown in FIG. 16) to be in the fluorescence observation mode, in accordance with operation to the operation switch 15 by the operator. FIG. 18 is a schematic illustration of the video signal transmission in the fluorescence observation mode. In this mode, a W video signal and an F video signal are alternately and repeatedly output from the CCD 14. These video signals are converted into W video data and F video data, respectively, as they are processed by the pre-processing circuit 521 and the A/D converter 522. Therefore, the A/D converter 522 alternately outputs the W video data and the F video data. During the period in which the A/D converter 522 outputs the W video data, the W video data is stored in the second memory 524. Then, during the period in which the A/D converter 522 outputs the F video data, the F video data is stored in the first memory 523. In this mode, the third memory 525 is not used. The W video data and the F video data are then read out from the memories 524 and 523 respectively at predetermined timing, and subjected to digital-to-analog conversion by the D/A converters 527 and 526, respectively. Since the switches SW1 and SW2 are operated so as to be in the fluorescence observation mode in this time, to the second output terminal P2 and the third output terminal P3 is transmitted the W video signal which is output from the D/A converter 527 as it is, and to the first output terminal P1 is transmitted the video signal obtained by subtracting the F video signal which is output from the D/A converter 526 from the W video signal, as shown in FIG. 18. The video signals output from the output terminals P1, P2 and P3 are transmitted to the monitor 3 along with a synchronizing signal as diagnostic image signals. As a result, the monitor 3 displays a moving diagnostic image of the object under examination for the purpose of diagnosis.

If only the W video data were transmitted to the output terminals P1, P2 and P3, a monochromatic image of the object under examination that is irradiated with white light would be displayed on the screen of the monitor 3. However, in reality, the video signal obtained by subtracting the F video signal from the W video signal is transmitted to the first output terminal P1 as described above. Therefore, in the diagnostic image displayed on the monitor 3, a part of the object that are not generating autofluorescence is indicated as the monochromatic image. On the other hand, in the image displayed on the monitor 3, the part of the object that are generating autofluorescence are colored in accordance with the intensity of the autofluorescence. Thus, the doctor can recognize the profile of the object under examination and also the intensity distribution of the autofluorescence of the object by observing the diagnostic image displayed on the monitor. Specifically, the doctor can discriminate normal areas where the autofluorescence is intense and diseased areas where the autofluorescence is weak.

Although the autofluorescence generated from a living body is very weak, the period when the excitation light is emitted through the light distribution lens 11 is set longer than the period when the white light is emitted, as described above, so that the intensity level of the F video signal generated based on the autofluorescence is substantially equal to that of the W video signal. Thus, the F video signal is not over amplified, to be subtracted from the W video signal in generating the diagnostic video signal. Therefore, proper F video signal and therefore proper diagnostic video signal with a high S/N ratio can be obtained anytime. The diagnostic video signal makes the monitor 3 display a clear diagnostic image that is mostly free from noise. Then, the doctor can accurately diagnose the diseased portion by observing the displayed clear diagnostic image of the object under examination.

It should be noted that the intensity of the autofluorescence generated by healthy tissue can vary from place to place in a living body. Therefore, the chart H is preferably prepared for each part of the living body to be observed. Thus, the operator can perform the level regulation in a simple way each time a part of the living body to be observed is newly selected. It may alternatively be so arranged that the timing controller 51 adjust the "UV irradiation" period and the "W irradiation" period by shifting the timing of the start of the "W transfer" period.

As described above in detail, a video endoscope system according to the invention can adjust the time during which the object under examination is irradiated with excitation light, which raises the signal intensity of the video signal obtained based on the autofluorescence generated from the object under examination. Therefore, the image displayed on the basis of the video signal is clear and substantially free from noise. Thus, the diagnosis based on such an image will be highly reliable.

As described above in detail, a video endoscope apparatus according to the invention is adapted to make the time during which the object under examination is irradiated with excitation light relatively long. This is done to raise the signal intensity of the video signal obtained based on the self-fluorescence of the object under examination. Therefore, the image generated, based on the video signal, is clear and substantially free from noise. Thus, the diagnosis based on such an image will be highly reliable. No.2000-306430 (filed on Oct. 5, 2000) and No.2000-317847 (filed on Oct. 18, 2000), which are expressly incorporated herein by reference in its entirety.

We claim:

1. A video endoscope system comprising:
an illuminating optical system that guides light to an object under examination;
a light source unit that emits visible light and excitation light for exciting a living tissue of the object to cause fluorescence, and that alternately transmits the visible light and the excitation light to said illuminating optical system so that a period during which the excitation light is transmitted to the illuminating optical system is longer than a period during which the visible light is transmitted to the illuminating optical system;
an objective optical system that converges optical components of light coming from a surface of the object, other than the excitation light, to form an image of the object;
an image pickup device that picks up the image of the object formed by said objective optical system and converts the image into a video signal; and
a processor that generates a reference video signal based on the video signal obtained by said image pickup device during the period when the visible light is transmitted to said illuminating optical system, and that generates a fluorescence video signal based on the video signal obtained by the image pickup device during the period when the excitation light is transmitted to said illuminating optical system, said processor generating a video signal to be used for diagnosis by subtracting the fluorescence video signal from the reference video signal.

2. The video endoscope system according to claim 1, wherein
said light source unit includes
a visible light source for emitting the visible light;
an excitation light source for emitting the excitation light; and
a light source switching device which alternately selects the visible light emitted from said visible light source and the excitation light emitted from said excitation light source to transmit to said illuminating optical system.

3. The video endoscope system according to claim 2, wherein
said light source switching device includes
a first shutter for intermittently blocking the visible light emitted from said visible light source in an optical path of the visible light;
a second shutter for intermittently blocking the excitation light emitted from said excitation light source in an optical path of the excitation light; and
a shutter drive mechanism which makes the second shutter block the excitation light while the first shutter transmits the visible light, and which makes the first shutter block the visible light while the second shutter transmits the excitation light.

4. The video endoscope system according to claim 3, wherein
said first shutter is a rotary shutter which is a disk blocking the visible light, formed with a visible light transmitting part for transmitting the visible light in an area along its circumference;
said second shutter is a rotary shutter which is a disk blocking the excitation light, formed with an excitation light transmitting part for transmitting the excitation light in an area along its circumference;
said shutter drive mechanism causes the first and second shutters to rotate so as to put the excitation light transmitting part of said second shutter into the optical path of the excitation light while said first shutter blocks the visible light, and to put the visible light transmitting part of said first shutter into the optical path of the visible light while said second shutter blocks the excitation light.

5. The video endoscope system according to claim 4, wherein
a central angle of said excitation light transmitting part relative to a center of rotation of said second shutter is greater than a central angle of said visible light transmitting part relative to a center of rotation of said first shutter;
and wherein said shutter drive mechanism rotates said first and second shutters at same angular velocity as each other.

6. The video endoscope system according to claim 1, further comprising
a monitor for displaying an image based on the video signal output from said processor.

7. A video endoscope system, comprising:
an illuminating optical system that guides light to an object under examination;
a light source unit that emits visible light and excitation light for exciting a living tissue of the object to cause fluorescence, said light source unit alternately transmitting the visible light and the excitation light to said illuminating optical system, a period during which said light source unit transmits the visible light to the illuminating optical system and a period during which said light source unit transmits the excitation light to the illuminating optical system being adjustable;
an objective optical system that converges optical components of light coming from a surface of the object, other than the excitation light, to form an image of the object;
an image pickup device that picks up the image of the object formed by said objective optical system and converts the image into a video signal; and
a processor that generates a reference video signal based on the video signal obtained by said image pickup device during the period when the visible light is transmitted to said illuminating optical system, and a fluorescence video signal based on the video signal obtained by the image pickup device during the period when the excitation light is transmitted to said illuminating optical system, said processor generating a video signal to be used for diagnosis by subtracting the fluorescence video signal from the reference video signal.

8. The video endoscope system according to claim 7, wherein the period during which the excitation light is transmitted to said illuminating optical system and the period during which the visible is transmitted to said illuminating optical are adjusted so that a ratio of an intensity of the reference video image signal, obtained during a period when a predetermined object is irradiated with the visible light, to an intensity of the fluorescence video signal, obtained during a period when the predetermined object is irradiated with the excitation light, is a predetermined value, the predetermined object reflecting the visible light with a predetermined reflectance when illuminated with the visible light and causing fluorescence when irradiated with the excitation light with an intensity in proportion to an intensity of the excitation light.

9. The video endoscope system according to claim 8, wherein said light source unit includes a visible light source for emitting the visible light;

an excitation light source for emitting the excitation light; and a light source switching device which alternately selects the visible light emitted from said visible light source and the excitation light emitted from said excitation light source to transmit to said illuminating optical system and which can vary the period when the excitation light is transmitted to the illuminating optical system and the period when the visible light is transmitted to the illuminating optical system.

10. The video endoscope system according to claim 9, wherein said processor has a controller which controls said light source switching device so as to adjust the period when the excitation light is transmitted to the illuminating optical system and the period when the visible light is transmitted to the illuminating optical system in those way.

11. The video endoscope system according to claim 10, wherein said light source switching device includes a first shutter for intermittently blocking the visible light emitted from said visible light source in an optical path of the visible light;

a second shutter for intermittently blocking the excitation light emitted from said excitation light source in an optical path of the excitation light; and a shutter drive mechanism which makes the second shutter block the excitation light while the first shutter transmits the visible light, and which makes the first shutter block the visible light while the second shutter transmits the excitation light.

12. The video endoscope system according to claim 11, wherein said first shutter includes a first rotary shutter and a second rotary shutter, each of the first and second rotary shutters comprising a disk for blocking the visible light and a visible light transmitting part for transmitting the visible light in an area along a circumference of the disk, said first and second rotary shutters rotating coaxially and together with each other;

said second shutter includes a third rotary shutter and a fourth rotary shutter, each of the third and fourth rotary shutters comprising a disk for blocking the excitation light and an excitation light transmitting part for transmitting the excitation light in an area along a circumference of the disk, said third and fourth rotary shutters rotating coaxially and together with each other; and said shutter drive mechanism adjusts a peripheral length of a visible light transmitting area, which is an overlapping area of the visible light transmitting part of each of said first rotary shutter and said second rotary shutter, by changing relative phases of rotation between the first and second rotary shutters, and adjusts a peripheral length of an excitation light transmitting area, which is an overlapping area of the excitation light transmitting part of each of said third rotary shutter and said fourth rotary shutter, by changing relative phases of rotation between the third and fourth rotary shutters, said shutter drive mechanism rotating the respective rotary shutters such that the excitation light transmitting area of said third rotary shutter and said fourth rotary shutter is inserted into the optical path of the excitation light when said first rotary shutter and said second rotary shutter block the visible light, and that the visible light transmitting area of said first rotary shutter and said second rotary shutter is inserted into the optical path of the visible light when said third rotary shutter and said fourth rotary shutter block the excitation light.

13. The video endoscope system according to claim 7, further including a monitor for displaying an image based on the video signal output from said processor.

14. A video endoscope system comprising:

an illuminating optical system that guides light to an object under examination;

a light source unit that emits visible light and excitation light for exciting a living tissue of the object to cause fluorescence, and that alternately transmits the visible light and the excitation light to said illuminating optical system so that a period during which the excitation light is transmitted to the illuminating optical system is longer than a period during which the visible light is transmitted to said illuminating optical system;

an objective optical system that converges optical components of light coming from a surface of the object, other than the excitation light, to form an image of the object;

an image pickup device that picks up the image of the object formed by said objective optical system and converts the image into a video signal; and a processor that generates a reference video signal based on the video signal obtained by said image pickup device during the period when the visible light is transmitted to said illuminating optical system, and that generates a fluorescence video signal based on the video signal obtained by the image pickup device during the period when the excitation light is transmitted to said illuminating optical system;

said light source unit comprising:

a wheel that rotates around an axis parallel to a light path of the visible light, the wheel comprising a plurality of color filters positioned along a circumference of the wheel, the filters including a blue filter for transmitting only blue light, a green filter for transmitting only green light and a red filter for transmitting only red light; and a wheel moving mechanism that moves the wheel between a first position, in which the plurality of color filters are sequentially inserted into the light path of the visible light between a light source switching device and said illuminating optical system as the wheel rotates, and a second position, in which the wheel is located out of the light path of the visible light, said processor comprising a controller for controlling the light source switching device and the wheel moving mechanism;

said processor generating a diagnostic video signal by subtracting the fluorescence video signal from the reference video signal in a fluorescent observation mode, in which the controller controls the light source switching device to alternately select the visible light and the excitation light to transmit to said illuminating optical system, and controls the wheel moving mechanism to move the wheel to the second position; and wherein said processor generates a plurality of color video signals, corresponding to the plurality of color filters, based on video signals obtained by said image pickup device during periods when the corresponding color filters are inserted into the light path of the visible light, and further generates an ordinary video signal representing a color image of the object under examination based on each of the color video signals in an ordinary observation mode, in which the controller controls the light source switching device to select only the visible light to transmit to said illuminating optical system and controls the wheel moving mechanism to move the wheel to the first position.

15. A video endoscope system comprising:

an illuminating optical system that guides light to an object under examination;

a light source unit that emits visible light and excitation light for exciting a living tissue of the object to cause fluorescence, and that alternately transmits the visible light and the excitation light to said illuminating optical system, a period during which the excitation light is transmitted to the illuminating optical system and a period during which the visible light is transmitted to said illuminating optical system being adjustable;

an objective optical system that converges optical components of light coming from a surface of the object, other than the excitation light, to form an image of the object;

an image pickup device that picks up the image of the object formed by said objective optical system and converts the image into a video signal; and a processor that generates a reference video signal based on the video signal obtained by said image pickup device during the period when the visible light is transmitted to said illuminating optical system, and that generates a fluorescence video signal based on the video signal obtained by the image pickup device during the period when the excitation light is transmitted to said illuminating optical system;

said light source unit comprising:

a wheel comprising a plurality of color filters positioned along a circumference of the wheel, the filters including a blue filter for transmitting only blue light, a green filter for transmitting only green light and a red filter for transmitting only red light; and a wheel driver that rotates the wheel and that moves the wheel between a first position, in which the plurality of color filters are sequentially and repeatedly inserted into an optical path of the visible light, and a second position, in which the wheel is retracted from the optical path of the visible light;

said processor setting said light source unit in one of a fluorescence observation state, in which the visible light and the excitation light are alternately transmitted to said illuminating optical system, and an ordinary observation state, in which only the visible light is transmitted to said illuminating optical system; and wherein, when said light source unit is set in the fluorescence observation state, said processor controls the wheel driver to move the wheel to the second position and generates a video signal to be used for diagnosis by subtracting the fluorescence video signal from the reference video signal, and when said light source unit is set in the ordinary observation state, said processor controls the wheel driver to rotate the wheel and to move the wheel to the first position and generates a plurality of color video signals respectively based on signals obtained by said image pickup device during periods when the corresponding one of the plurality of color filters are inserted into the optical path of the visible light, said processor generating an ordinary video signal representing a color image of the object under examination based on the plurality of color video signals.

* * * * *